United States Patent
Lam et al.

(10) Patent No.: US 10,695,401 B2
(45) Date of Patent: Jun. 30, 2020

(54) USE OF VIMENTIN IN THE MODULATION OF ACUTE INFLAMMATION AND THROMBOSIS

(71) Applicant: Baylor College of Medicine, Houston, TX (US)

(72) Inventors: Fong Wilson Lam, Houston, TX (US); Qi Da, Houston, TX (US); Miguel A. Cruz, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/465,071

(22) PCT Filed: Nov. 30, 2017

(86) PCT No.: PCT/US2017/064051
§ 371 (c)(1),
(2) Date: May 29, 2019

(87) PCT Pub. No.: WO2018/102603
PCT Pub. Date: Jun. 7, 2018

(65) Prior Publication Data
US 2020/0061153 A1    Feb. 27, 2020

Related U.S. Application Data

(60) Provisional application No. 62/428,832, filed on Dec. 1, 2016.

(51) Int. Cl.
*A61K 38/00* (2006.01)
*A61K 38/17* (2006.01)
*A61P 11/00* (2006.01)

(52) U.S. Cl.
CPC .......... *A61K 38/1709* (2013.01); *A61P 11/00* (2018.01)

(58) Field of Classification Search
None
See application file for complete search history.

(56) References Cited

U.S. PATENT DOCUMENTS

2004/0259112 A1    12/2004    Georges et al.
2012/0021974 A1    1/2012    Pall et al.

FOREIGN PATENT DOCUMENTS

WO    2008/093076 A2    8/2008
WO    WO-2008093076 A2 *    8/2008    ........... G01N 33/564

\* cited by examiner

*Primary Examiner* — Jeanette M Lieb
(74) *Attorney, Agent, or Firm* — Norton Rose Fulbright US LLP

(57) ABSTRACT

Embodiments of the disclosure include methods and compositions for treating or preventing acute inflammation using soluble vimentin. In specific embodiments, a vimentin derivative comprising the rod domain is utilized for treating or preventing any disease in which a decrease in leukocyte adhesion is therapeutic. In specific embodiments, a fragment of vimentin that comprises part or all of the rod domain is employed.

10 Claims, 19 Drawing Sheets
Specification includes a Sequence Listing.

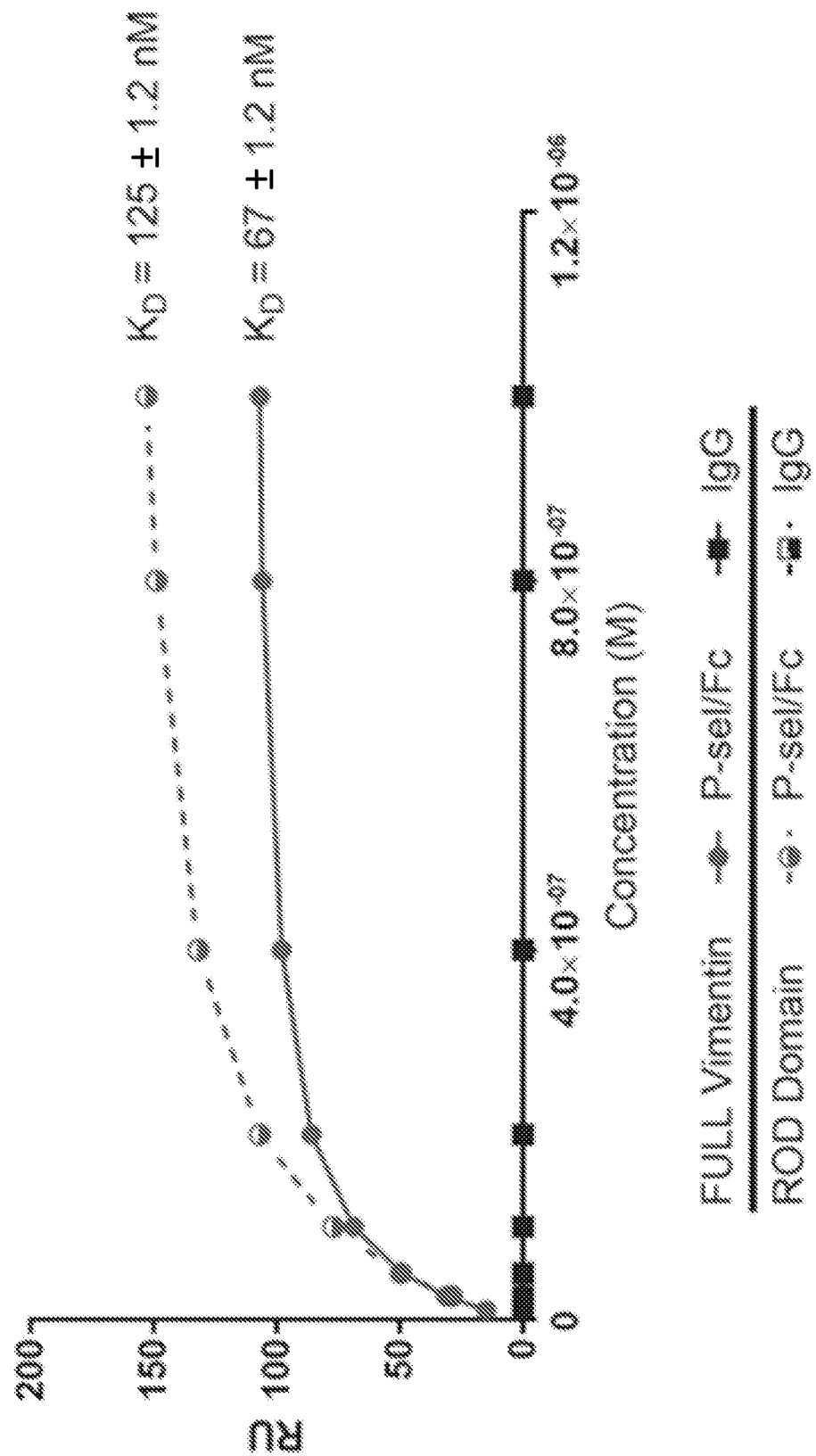

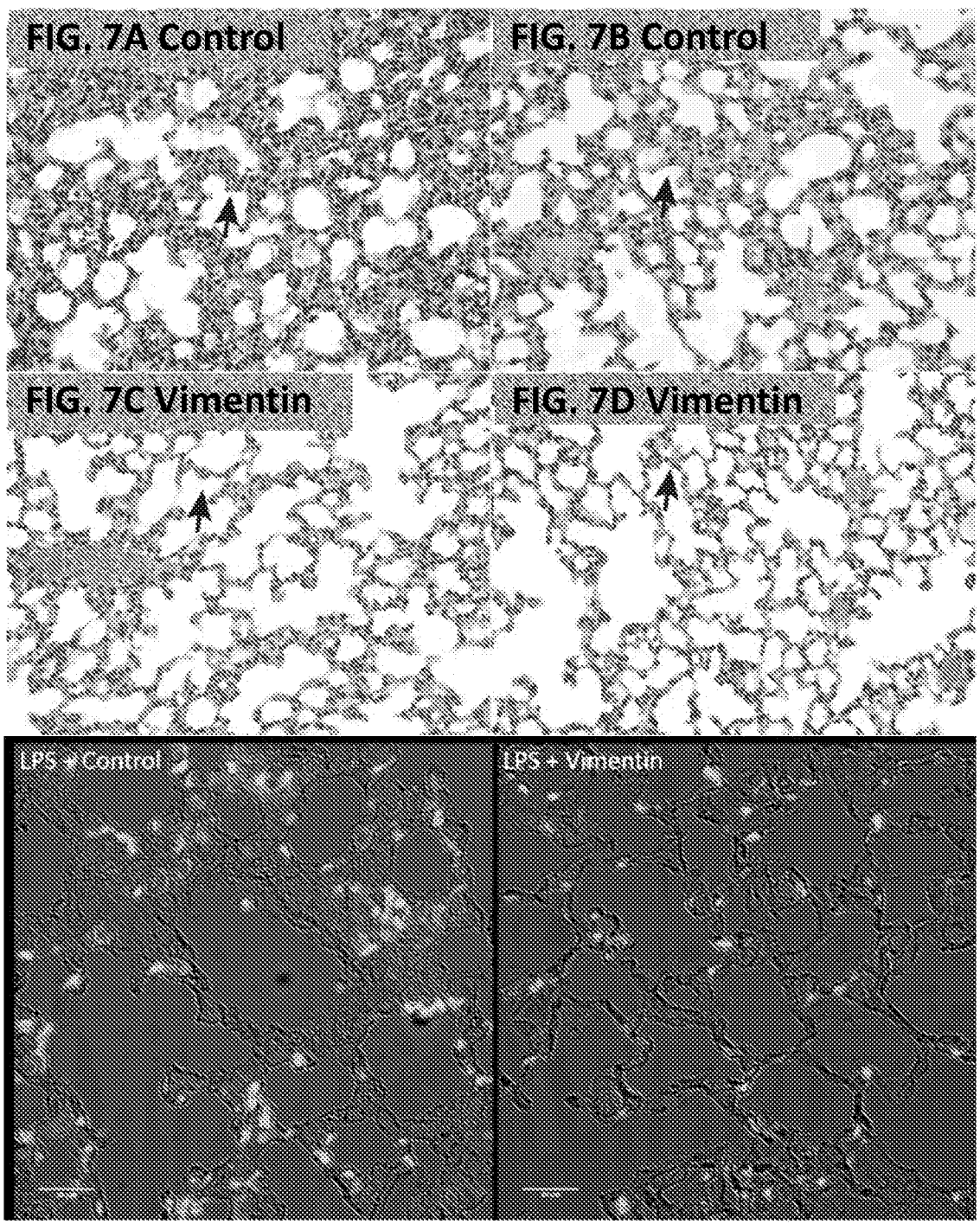

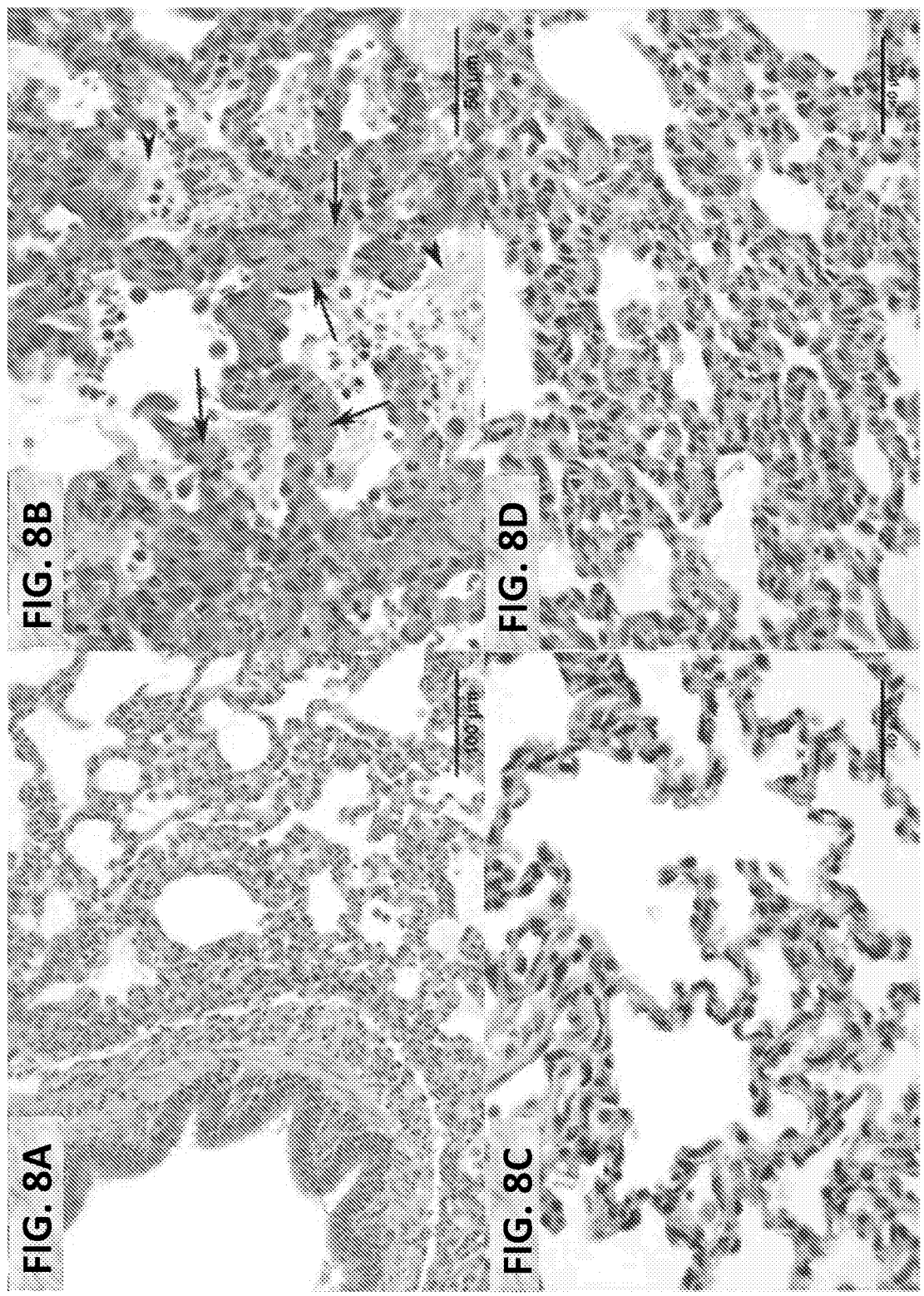

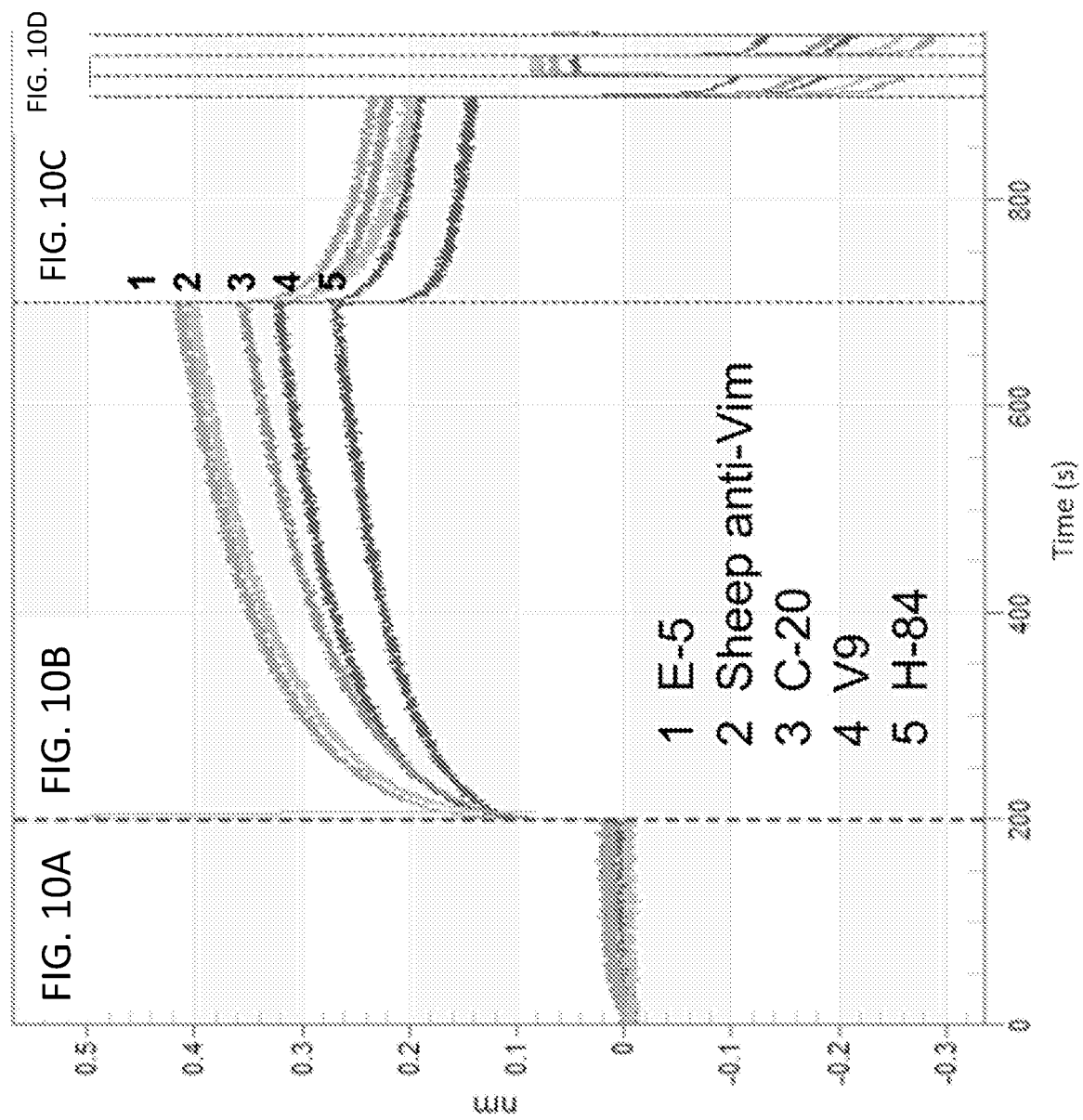

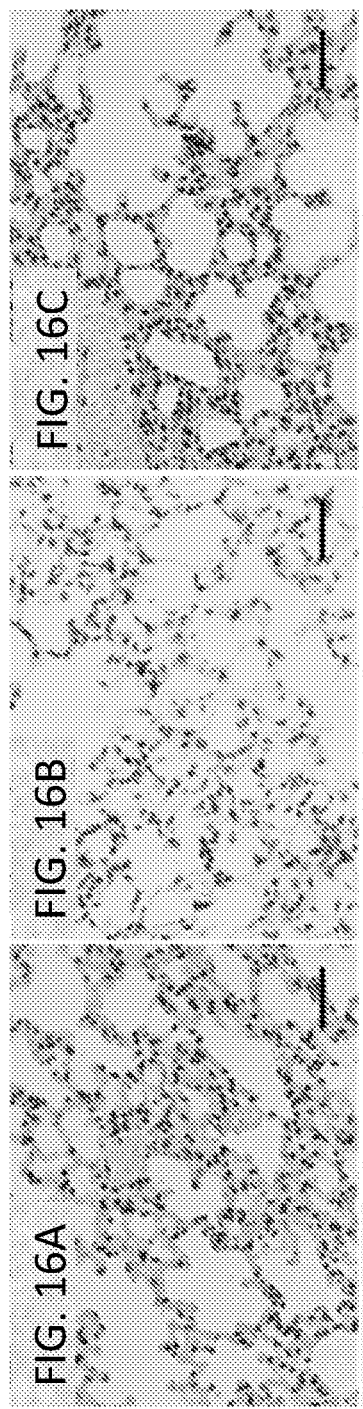
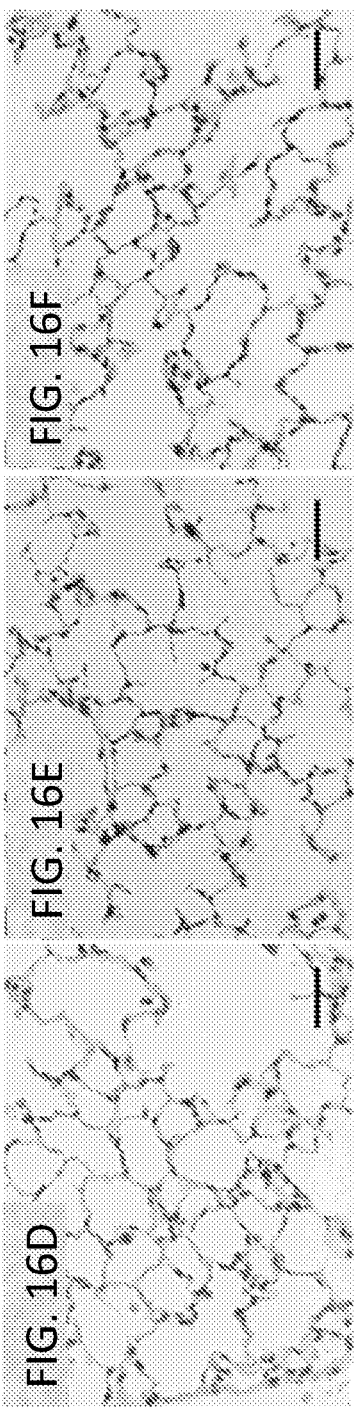
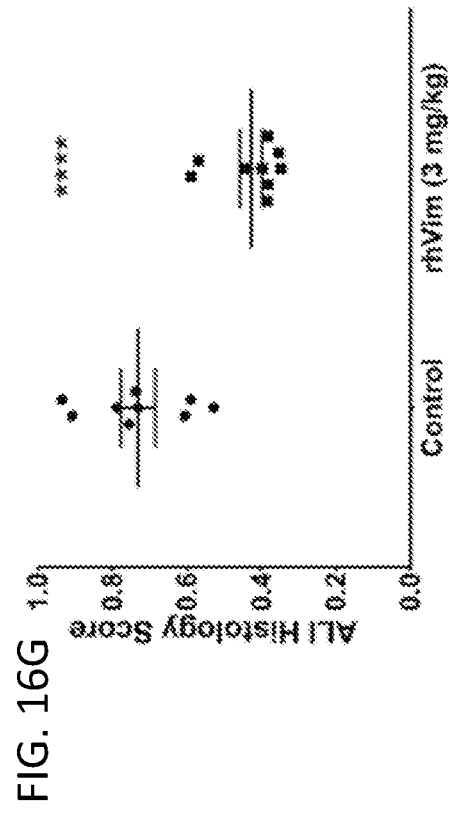

USE OF VIMENTIN IN THE MODULATION OF ACUTE INFLAMMATION AND THROMBOSIS

This application is a national phase application under 35 U.S.C. § 371 that claims priority to International Application No. PCT/US2017/064051 filed Nov. 30, 2017, which claims priority to U.S. Provisional Patent Application Ser. No. 62/428,832, filed Dec. 1, 2016, all of which are incorporated herein by reference in their entirety.

STATEMENT REGARDING FEDERALLY SPONSORED RESEARCH OR DEVELOPMENT

This invention was made with government support under 5R01GM112806 awarded by National Institutes of Health and funds provided by the Department of Veterans Affairs. The government has certain rights in the invention.

TECHNICAL FIELD

Embodiments of the disclosure include at least the fields of cell biology, molecular biology, and medicine.

BACKGROUND

Acute lung injury (ALI), and its severe form, acute respiratory distress syndrome (ARDS), are devastating conditions that affect approximately ~200,000 persons per year in the United States and represent ~10% of intensive care unit admissions worldwide (1,2). Despite advancements in intensive care, mortality from ALI/ARDS remains high, reaching 35-40%. ALI/ARDS is a type of pathologic inflammation, whereby injury to the lungs may be due to an initial insult elsewhere in the body, leading to activation of the immune system (inflammation). In fact, approximately 30% of patients with ARDS have extra-pulmonary causes. One such example is secondary ALI/ARDS because of the inflammatory state of sepsis (3-5) (reviewed in (6)).

Integral to the initiation of inflammation is the interaction and adhesion of leukocytes to platelets and vascular endothelium. These early steps are mediated through cell surface adhesion molecules on the leukocytes to counter-receptors on platelets and endothelium (7-12). In most cases, the presence of inflammation plays an important role in the maintenance of health, such as in infection (5) and wound healing (13). However, in pathologic inflammation, these processes may lead to tissue injury and organ dysfunction at sites distant from the initial insult. Therefore, blocking leukocyte recruitment into otherwise healthy organs could have a beneficial role in attenuating pathologic inflammation, such as ALI and ARDS.

The present disclosure provides a solution to the need for treatment of certain medical conditions, including at least ALI and ARDS, for example.

BRIEF SUMMARY

Pathologic inflammation plays a central role in many disease states, leading to morbidity and mortality, and embodiments of the disclosure concern methods of prevention or treatment thereof. An early event in inflammation is the capture and adhesion of leukocytes to the microvascular endothelium that can lead to progressive organ injury. Embodiments of the disclosure concern methods and compositions for treating acute inflammation, including that associated with any medical condition. Particular embodiments of the disclosure utilize vimentin, including soluble vimentin, for treating acute inflammation or any medical condition in which the blocking of leukocyte adhesion to certain cells or tissues is beneficial. In specific embodiments, the medical condition is treated, or at least one symptom is improved upon, following blockage of leukocyte adhesion to platelets, endothelial cells, blood vessels, and so forth. In specific embodiments, the medical condition is not chronic inflammation.

In specific embodiments, vimentin or functionally active fragments or derivatives thereof results in an improvement of at least one symptom of a medical condition in which inflammation is involved, including at least acute inflammation. In particular embodiments, the medical condition is acute lung injury or acute respiratory distress syndrome, for example.

In one embodiment, there is a method of treating or preventing acute inflammation in an individual, comprising the step of delivering to the individual a therapeutically effective amount of vimentin or a functionally active fragment and/or functionally active variant thereof. The acute inflammation may comprise acute lung injury, secondary lung injury, acute respiratory distress syndrome, ischemia/reperfusion injury, trauma, sepsis, pancreatitis, drug-induced organ injury, or a combination thereof. In specific cases, the fragment of vimentin comprises N-terminal head domain, C-terminal tail domain, α-helical coiled-coil rod domain, or a combination thereof. The fragment may comprise the N-terminus, the C-terminus, both the N-terminus and C-terminus, or neither of the N-terminus or C-terminus. In some cases, the fragment or derivative is at least 70, 75, 80, 85, 90, 91, 92, 93, 94, 95, 96, 97, 98, or 99% identical to SEQ ID NO:1. In specific embodiments, the variant comprises 1, 2, 3, 4, 5, or more variations compared to SEQ ID NO:1, SEQ ID NO:2, SEQ ID NO:3, SEQ ID NO:5, or SEQ ID NO:7. The fragment may comprise amino acids 96-407 of SEQ ID NO:1, in certain cases. An individual may be provided a second therapy for the medical condition being treated with vimentin. Any method of the disclosure may further comprise diagnosis of the medical condition.

In specific embodiments, vimentin is delivered to the individual intravenously, intradermally, transdermally, intrathecally, intraarterially, intraperitoneally, intranasally, intravaginally, intrarectally, topically, intramuscularly, subcutaneously, mucosally, orally, topically, locally, by inhalation, by injection, by infusion, via catheter, and/or via lavage, and the vimentin may be delivered to the individual once a day, more than once a day, more than once a week, more than once a month, or more than once a year. The vimentin may be delivered to the individual once or multiple times, and in any case the vimentin may be provided to an individual by constant infusion.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of opera-

BRIEF DESCRIPTION OF THE DRAWINGS

(FIG. 3A) 20× image of leukocytes rolling in a cremaster venule. Colored lines are shown to highlight rolling analyses. (FIG. 3B) WBC rolling in Vim$^{-/-}$ mice was significantly slower than WT controls. *$p<0.05$, n=4 mice/grp.

FIG. 4A shows a 10× image of mepacrine-labelled WBC rolling and adhering to fibrinogen-coated channels in the presence (top) and absence (bottom) of vimentin. Scale bar is 50 µm. FIG. 4B shows that srhVim decreases leukocyte adhesion to fibrinogen-coated plates. **$p<0.01$; ^$p<0.01$, n=3 paired subjects FIGS. 5A and 5B. (FIG. 6C) Surface plasmon resonance (BIACore) was used to calculate the KD of both full-length Vimentin (solid line) and a portion of vimentin (rod domain; dashed line). There was saturation binding of vimentin to P-sel/Fc but no binding to Ig control.

FIGS. 7A-7D providings hematoxylin and eosin stain of lungs from endotoxemic mice (4 days) that were treated with either vehicle control (FIGS. 7A & 7B) or srhVim (FIGS. 7C & 7D). Mice treated with srhVim had decreased leukocytic infiltration into the lungs and thinner alveolar septa than the control group (arrows). Neutrophilic infiltration was confirmed using anti-neutrophil (Ly-6G; green) antibodies, with increased neutrophils in control mice (bottom left) than vimentin-treated mice (bottom right). Green=anti-Ly6G (neutrophils). Blue=DAPI (cell nuclei); grey=brightfield. Scale bar=20 microns.

FIGS. 8A-8D demonstrate hematoxylin and eosin stain of lungs from endotoxemic piglets. (FIGS. 8A & 8B) and MRSA bacteremia (FIGS. 8C & 8D). (FIG. 8A) Low powered field in showing increased cellularity. (Scale bar=100 µm) (FIG. 8B) High powered field showing fibrin deposition into the capillaries (arrows) and alveolar spaces (arrowhead). (FIG. 8C) There are also neutrophils and erythrocytes seen within the alveoli. (Scale bar is 50 µm) (FIGS. 8C & 8D) High powered field showing that, as compared to control piglets (FIG. 8C), there is increased leukocyte infiltrate in piglets exposed to MRSA bacteremia (FIG. 8D). Scale bar =40 µm.

FIGS. 10A-10D demonstrate that biolayer interferometry was performed with immobilized anti-vimentin antibodies (H-84, V9, C-20, E-5, and sheep anti-Vim). The phases of measurement are shown as (FIG. 10A) baseline in DPBS, (FIG. 10B) association phase, (FIG. 10C) dissociation phase, and (FIG. 10D) regeneration of antibodies. A positive shift in wavelength (nm) denotes binding of rhVim to immobilized antibodies.

(FIG. 11A) Representative fluorescence image shows adhered mepacrine-labeled leukocytes. (FIG. 11B) The addition of rhVim decreases leukocyte adhesion under venous shear stress (2 dyn/cm2541) in whole blood. Compared to control *$p<0.05$ as total PMN per field, n=3 paired subjects FIGS. 12A-12D provide fluorescence images of mepacrine-labeled isolated PMN flowing over (FIG. 12A) fibrin (ogen), (FIG. 12B) isolated platelets, or (FIG. 12C) glass (no coating).

FIG. 13A shows that the addition of rhVim decreased isolated PMN adhesion to immobilized platelet monolayers under venous shear stress (2 dyn/cm2550) in a dose-dependent fashion. In FIG. 13B, blocking antibodies to P-selectin and PSGL-1 also reduced isolated PMN adhesion to immobilized platelets. This effect was not further enhanced when the blocking antibodies were combined with rhVim 5 µg/mL. Compared to control, $p<0.01$ and *$p<0.005$, n=5 repeated subjects.

FIG. 14A provides A pseudo-colored fluorescence image of isolated PMN (bright green) flowing over IL-1β-stimulated HUVEC monolayers. In FIG. 14B, the addition of rhVim decreased isolated neutrophil adhesion to IL-1β-stimulated HUVEC under venous shear stress (2 dyn/cm2558). Compared to control, *$p<0.05$, n=6 paired subjects. FIG. 14C shows that rhVim significantly decreased isolated PMN adhesion to and (FIG. 14D) increased mean rolling velocity over IL-1β-stimulated HUVEC as compared to both vehicle control and boiled rhVim. *$p<0.05$, n=3 repeated subjects. (FIG. 14E) The addition of rhVim to whole blood also decreased WBC adhesion to IL-1β-stimulated HUVEC. Compared to control, **$p<0.01$, n=4 repeated subjects.

FIG. 15A shows that rhVim decreases isolated neutrophil adhesion to and (FIG. 15B) increased mean rolling velocity over immobilized P-sel/Fc under venous shear stress (2 dyn/cm2566). Compared to control, *$p<0.05$, $p<0.01$, *$p<0.005$, n=4 repeated subjects. FIG. 15C shows that rhVim preferentially bound to immobilized P-sel/Fc and does not to PSGL-1/Fc.

FIGS. 16A-16G show representative H&E sections of lungs from C57Bl/6 mice receiving intraperitoneal LPS after being treated with vehicle control (FIGS. 16A-16C) or intraperitoneal rhVim (FIGS. 16D-16F). Note the thicker alveolar walls and increased neutrophilic infiltration into the lungs in mice receiving vehicle control. (FIG. 16G) rhVim-treated mice had significantly lower ALI scores than the vehicle controls. ****$p<0.0001$, n=9 mice/grp. Scale bar=40 µm.

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the disclosure may consist of or consist essentially of one or more elements, method steps, and/or methods of the disclosure. It is contemplated that any method or composition described herein can be implemented with respect to any other method or composition described herein.

The phrase "effective amount" as used herein means that amount of a compound, material, or composition comprising a compound of the present disclosure that is effective for producing some desired effect, e.g., inhibiting leukocyte adhesion to particular cells or tissues. One of skill in the art recognizes that an amount may be considered effective even if the medical condition is not totally eradicated but improved partially. For example, the medical condition may be halted or reduced or its onset delayed, a side effect from the medical condition may be partially reduced or completed eliminated, and so forth. The effective amount may also be referred to as a therapeutically effective amount.

As used herein, an "individual" is an appropriate individual for the method of the present invention. A subject may be a mammal and in specific embodiments is any member of the higher vertebrate class Mammalia, including humans. Examples of mammals are humans, cats, dogs, cows, mice, rats, horses, sheep, pigs and chimpanzees. Subjects may also be referred to as "patients" or "subjects". The individual may be of any gender, race, or age.

I. General Embodiments of the Disclosure

Figure 1:
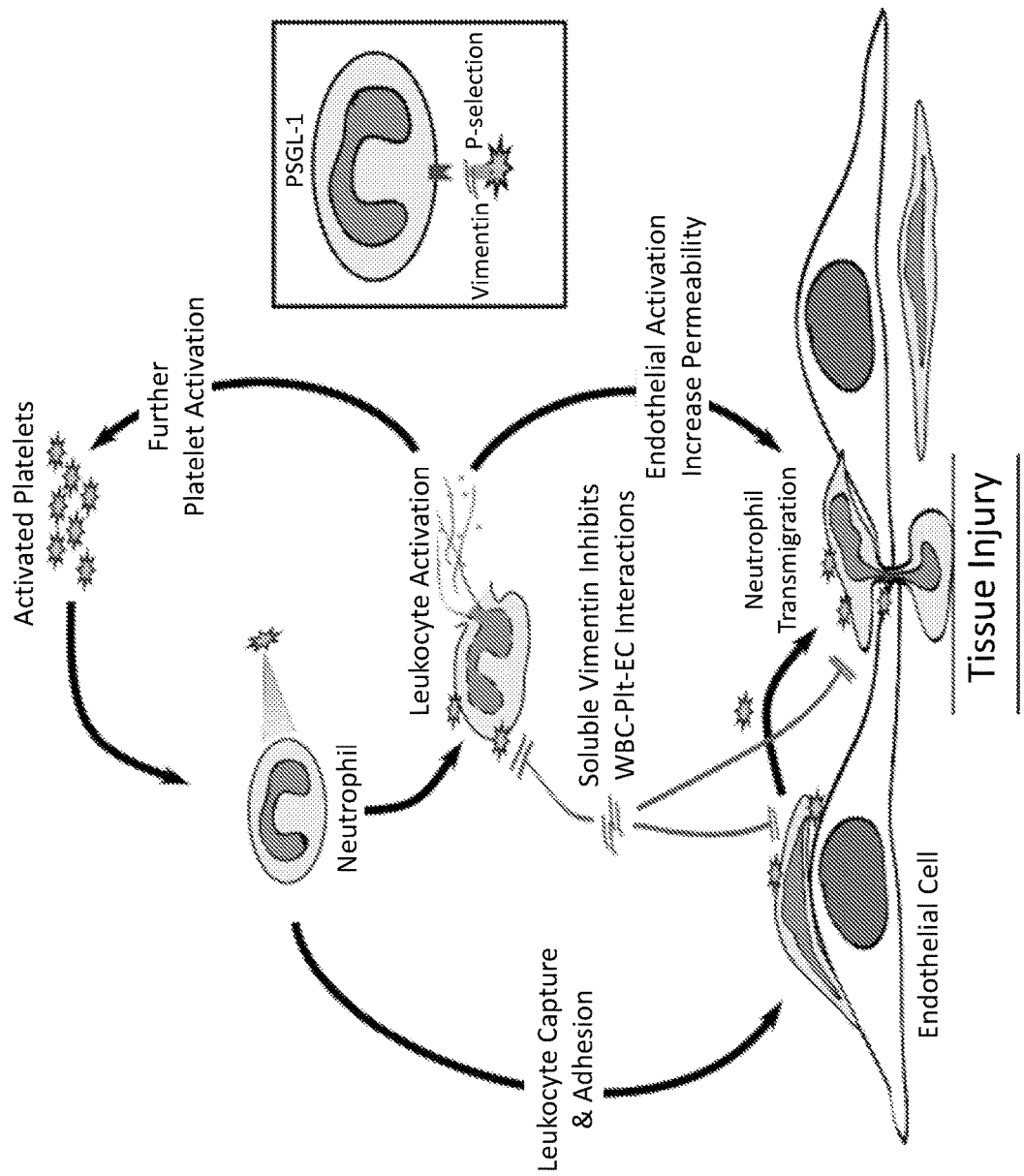
FIG. 1 shows one embodiment for a mechanism, soluble recombinant human vimentin (srhVim) may decrease tissue injury by blocking leukocyte adhesion and transmigration via blocking P-selectin-PSGL-1 interactions.

In particular embodiments, the disclosure concerns methods and compositions that modulate leukocyte trafficking in an individual, including leukocyte interaction with certain cells and/or tissues. One way to block leukocyte interaction with platelets and endothelium is through inhibiting the binding of leukocyte surface adhesion molecules to those on platelets and endothelium. Vimentin is an intracellular protein that is important for maintaining the cytoskeleton as well as intracellular transport. It is primarily located within mesenchymal cells but has also been reported on the surface of cells (14) as well as secreted into the plasma (15). As described herein, soluble recombinant human vimentin (srhVim) blocks leukocyte adhesion to both platelets and endothelial cells through binding to P-sel (FIG. 1), as an example of a mechanism. Furthermore, intravital microscopy data shows that leukocyte rolling in venules is slower in mice deficient in vimentin than wildtype, congruent with in vitro data. Finally, data in endotoxemic mice indicate that mice receiving srhVim had less leukocytic infiltrate into the lungs and improved activity.

In certain aspects, leukocyte trafficking is related to inflammatory processes, including acute inflammatory processes. Acute inflammation is associated with a variety of medical conditions, including at least ALI and ARDS. In particular embodiments of the disclosure, there is a decrease morbidity and mortality from ALI and ARDS by modulating leukocyte trafficking, especially because there are no effective therapies to prevent or treat this disease. Without wishing to be bound by theory, srhVim decreases acute lung injury by blocking leukocytic infiltration into the lungs. Thus, by modulating inflammation, one can reduce morbidity and mortality from ALI/ARDS, as well as other forms of pathologic inflammation, such as ischemia/reperfusion injury.

II. Vimentin Compositions

In embodiments of the disclosure, there are compositions that encompass part or all of vimentin. Although the vimentin may be from any mammal, including mice, rat, chimpanzee, dog, cat, cow, pig, and so forth, but in specific embodiments the vimentin is from human. This is because the vimentin sequence homology between different animals is high. Although the vimentin composition may be isolated from a mammal (and may or may not be modulated thereafter), in specific embodiments the vimentin composition is synthetically generated, such as by recombinant means. In specific embodiments, the vimentin is soluble, as opposed to being cell surface vimentin or intracellular vimentin. The vimentin may be synthetically produced, in certain cases. The vimentin may be soluble recombinant human vimentin (srhVim) or naturally occurring vimentin. In particular cases, the vimentin is administered exogenously (and therefore external to cells). In specific embodiments the vimentin is recombinant. In some cases, the vimentin is in monomer, dimer, or tetramer form. In certain cases the vimentin is glycosylated, whereas in other cases it is not glycosylated.

Figure 4A:
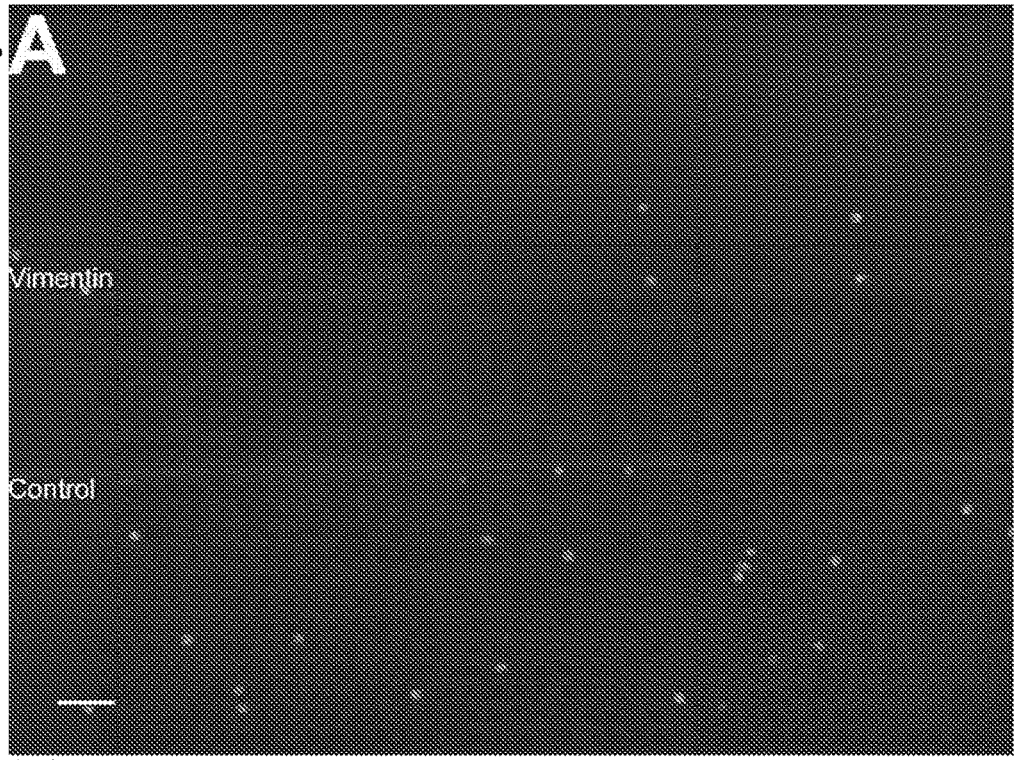
FIGS. 4A and 4B.
Figure 4B:
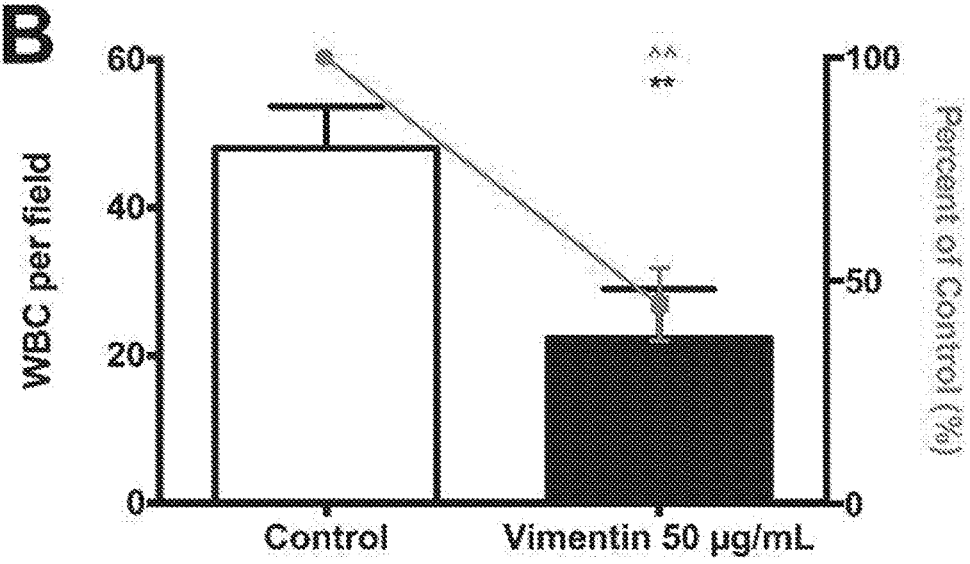
Figure 5A:
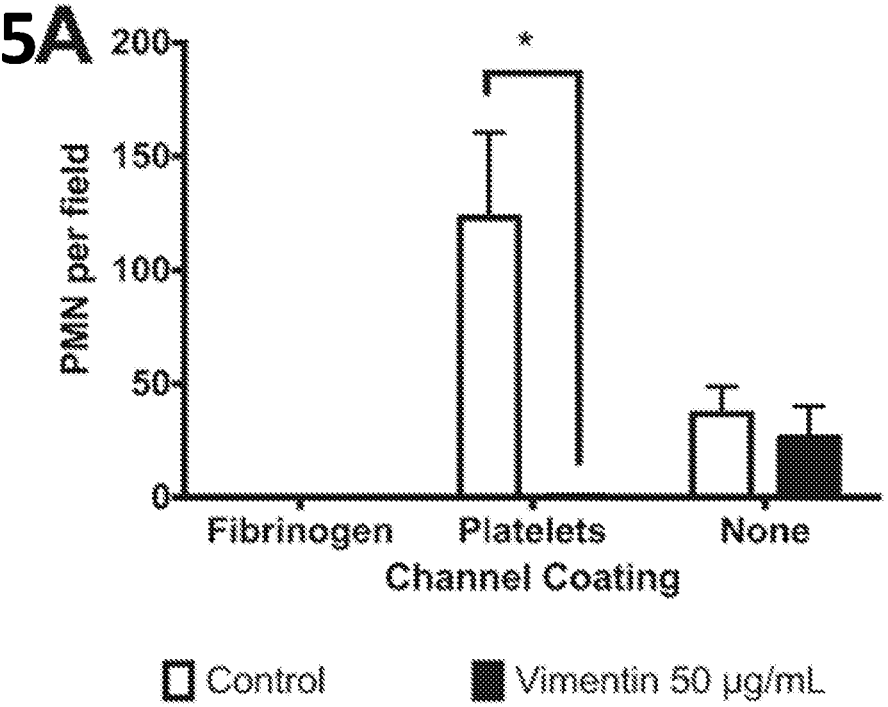
FIG. 5A demonstrates that srhVim decreases PMN adhesion to immobilized platelets (n=3 paired subjects) in a (FIG. 5B) dose-dependent fashion. *$p<0.05$, $p<0.01$; *$p<0.001$ n=5 repeated subjects FIGS. 6A-6C.
Figure 5B:
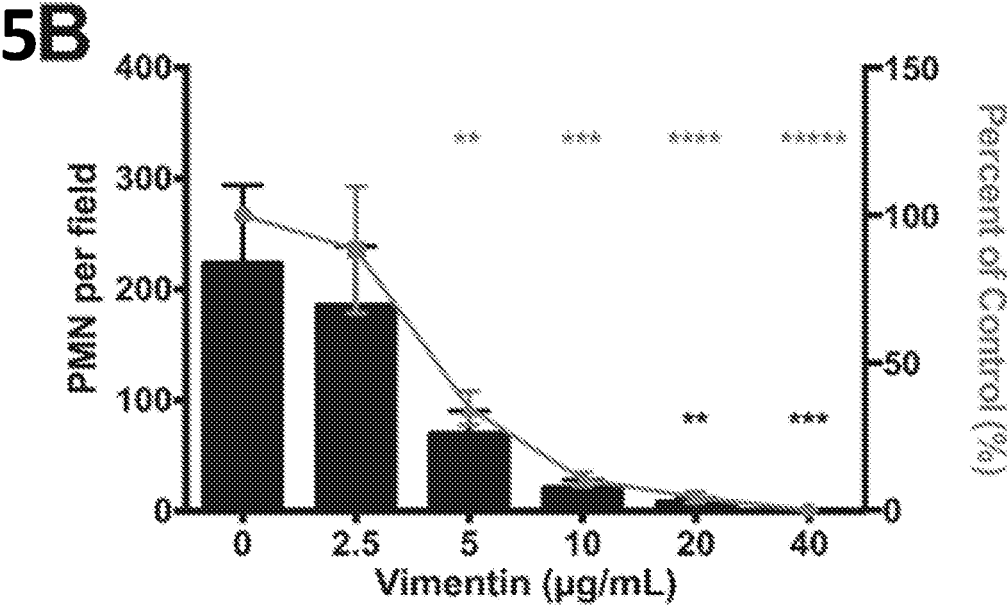
Figure 6A:
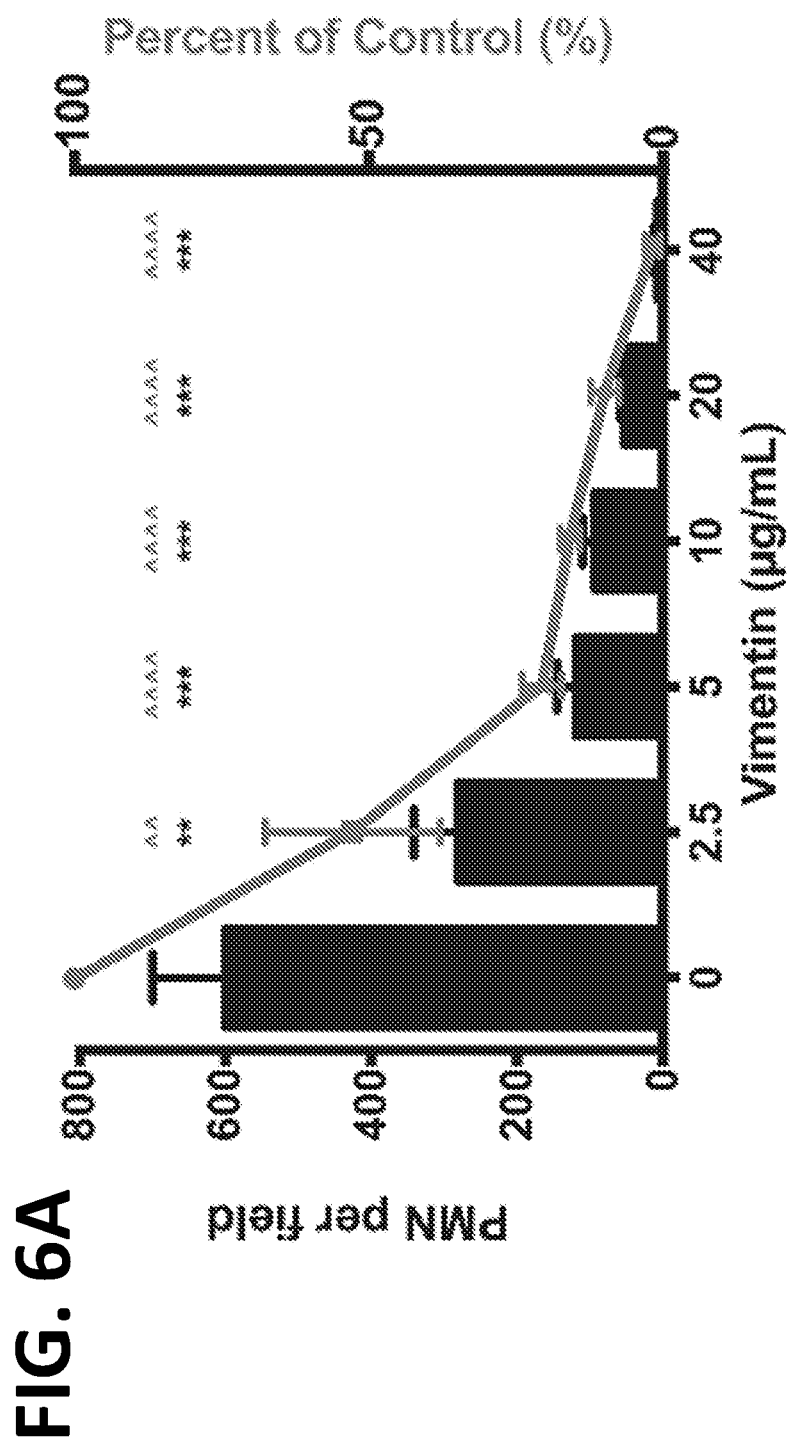
FIG. 6A shows that srhVim blocks PMN adhesion to immobilized P-sel/Fc protein in a dose-dependent fashion $p<0.01$; *$p<0.001$; n=4 repeated subjects).
Figure 6B:
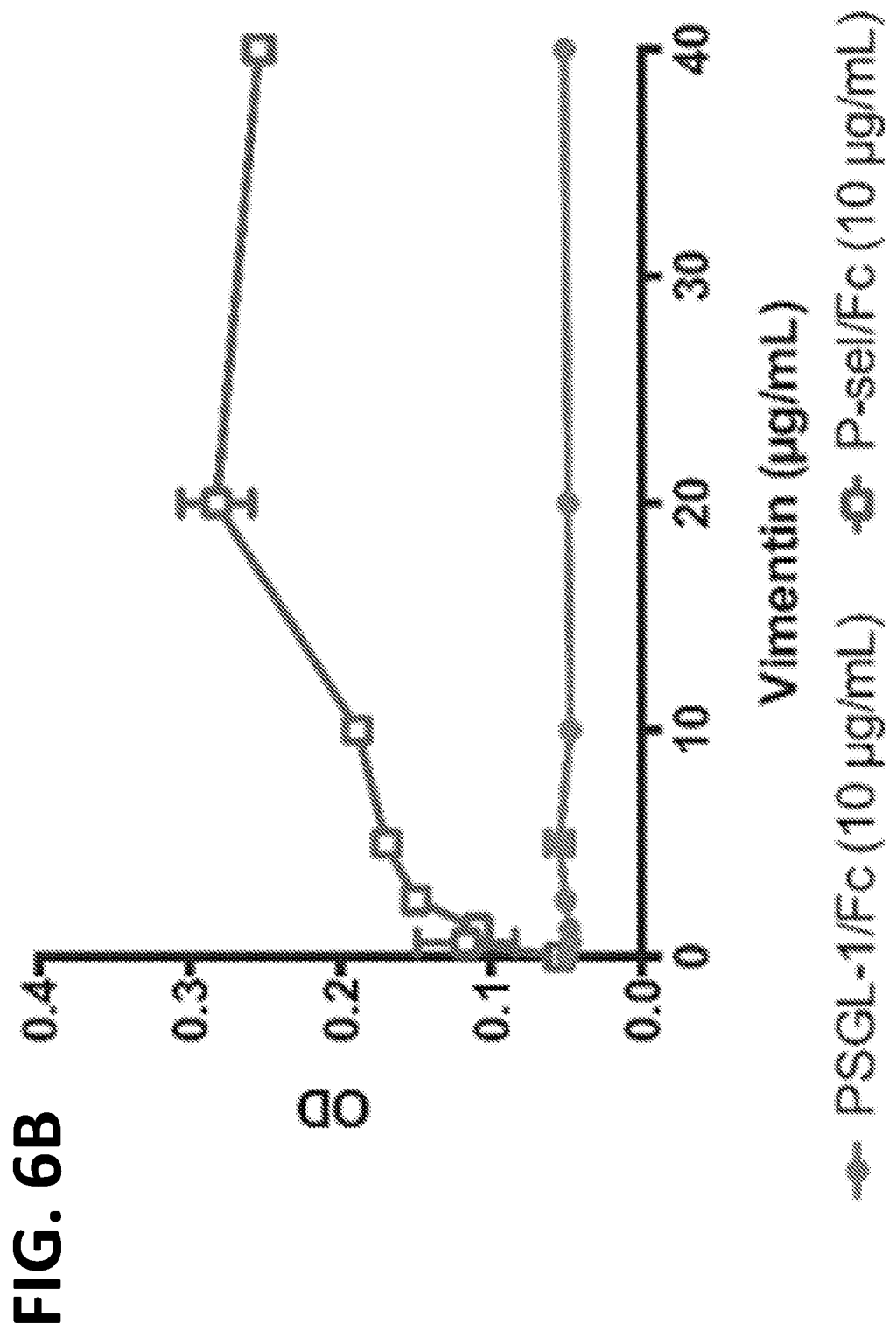
FIG. 6B shows that ELISA binding saturation curve. srhVim preferentially binds to P-sel/Fc (open squares) and does not bind PSGL-1/Fc.

In particular embodiments, the vimentin composition comprises the entirety of SEQ ID NO:1, although in other embodiments the vimentin composition may comprise a functionally equivalent variant of SEQ ID NO:1. The term "functionally equivalent variant" refers to a polynucleotide or polypeptide sequence that has been modified by substitution, insertion or deletion of one or more (e.g. 1, 2, 3, 4, 5, 6, 7, 8, 9 10) nucleotides or one or more (e.g. 1, 2, 3, 4, 5, 6, 7, 8, 9, 10) amino acids, respectively, but that has substantially the same or better activity as the reference sequence. Function of a polypeptide may be assessed experimentally, for example, by determining activity in an in vitro or in vivo experiment. Whether or not a given polypeptide or polynucleotide is "functional" may be determined by first selecting an appropriate function to assess. The functionality of vimentin and/or a variant or derivative may be assessed as the following: (1) in vitro testing to bind to cell surface receptors, such as but not limited to P-selectin, E-selectin, PSGL-1, etc., as described herein (FIGS. 6B and 6C); (2) in vitro testing of srhVim or its components on WBC rolling and adhesion to other cell types, such as but not limited to endothelial cells, platelets, cell adhesion molecules as described (FIGS. 4-6); (3) in vivo testing of vimentin on decreasing inflammation in diseases related to pathologic inflammation, such as but not limited to ALI/ARDS, sepsis as previously described (FIG. 7). In some cases, a functional molecule may be one that exhibits the desired function to a statistically significant degree (e.g. $p<0.05$; $<0.01$; $<0.001$). As a reference sequence, a vimentin polypeptide sequence is in the National Center for Biotechnology Information's GenBank® database at Accession Number NP_003371.

NP_003371
(SEQ ID NO: 1)

```
  1 mstrsvssss yrrmfggpgt asrpsssrsy vttstrtysl gsalrpstsr slyasspggv 61 yatrssavrl rssvpgvrll qdsvdfslad aintefkntr tnekvelqel ndrfanyidk 121 vrfleqqnki llaeleqlkg qgksrlgdly eeemrelrrq vdqltndkar veverdnlae 181 dimrlreklq eemlqreeae ntlqsfrqdv dnaslarldl erkveslqee iaflkklhee 241 eiqelqaqiq eqhvqidvdv skpdltaalr dvrqqyesva aknlqeaeew ykskfadlse 301 aanrnndalr qakqesteyr rqvqsltcev dalkgtnesl erqmremeen faveaanyqd 361 tigrlqdeiq nmkeemarhl reyqdllnvk maldieiaty rkllegeesr islplpnfss 421 lnlretnlds lplvdthskr tlliktvetr dgqvinetsq hhddle
```

In some embodiments, a fragment of vimentin is utilized that comprises one or more specific domains of vimentin. In specific cases, the vimentin fragment utilizes the rod, tail, and/or head domains. For example, a vimentin composition may comprise, consist of, or consist essentially of the rod domain, the tail domain, or the head domain.

In specific embodiments, a vimentin composition comprises a fragment of vimentin that is at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, or 460 amino acids in length. In some embodiments, a vimentin composition comprises a fragment of vimentin that is no more than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, or 460 amino acids in length. As an alternative to, or in addition to, the fragment having a certain length, the fragment may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:1. In some cases, sequential fragments of variable lengths that may extend between domains, e.g., include aa70-120, aa390-420, etc. of SEQ ID NO:1 (but not limited to these regions).

In one embodiment, there is provided an isolated human vimentin polypeptide fragment comprising at least a functional portion of vimentin (SEQ ID NO:1), or a functionally equivalent fragment or derivative thereof. In some embodiments, the polypeptide comprises at least 10, 11, 12, 13, 14, 15, 16, 17, 18, 19, 20, 21, 22, 23, 24, 25, 26, 27, 28, 29, 30, 31, 37, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, or more contiguous amino acids of vimentin (SEQ ID NO: 1). In some embodiments, the functional derivative comprises 1, 2, 3, 4, or 5 amino acid differences, such as conservative amino acid modifications, compared to SEQ ID NO:1. The vimentin fragment may include an N-terminal and/or C-terminal truncation of SEQ ID NO:1, such as of 1, 2, 3, 4, 5, 6, 7, 8, 9, 10, 15, 20, 25, or more amino acids truncated from the N-terminal and/or C-terminal of SEQ ID NO:1.

In some embodiments, any vimentin polypeptide fragment is less than 425, 400, 375, 350, 325, 300, 275, 250, 200, 100, 90, 80, 70, 60, 50, 40, 30, 20, or 10 amino acids in length. In some embodiments any vimentin polypeptide fragment is between 10-450, 50-450, 100-400, or 200-300 amino acids in length. In some embodiments the polypeptide fragment is between 10-60, 20-60, 30-60, 40-60 or 50-60 amino acids in length.

In particular embodiments, a vimentin fragment comprises (or consists of or consists essentially of) amino acids 96-407 of SEQ ID NO:1, and the sequence of such a fragment (which is the rod domain) is as follows and as noted as SEQ ID NO:2:

(SEQ ID NO: 2)
```
fkntr tnekvelgel ndrfanyidk vrfleqqnki llaeleqlkg qgksrlgdly eeemrelrrq vdqltndkar veverdnlae dimrlreklq eemlqreeae ntlqsfrqdv dnaslarldl erkveslqee iaflkklhee eiqelqaqiq eqhvqidvdv skpdltaalr dvrqqyesva aknlqeaeew ykskfadlse aanrnndalr qakqesteyr rqvqsltcev dalkgtnesl erqmremeen faveaanyqd tigrlqdeiq nmkeemarhl reyqdllnvk maldieiaty rkllege
```

The vimentin head domain is as follows:

(SEQ ID NO: 3)
MFGGPGTASRPSSSRSYVTTSTRTYSLGSALRPSTSRSLYASSPGGVYAT

RSSAVRLRSSVPGVRLLQDSVDFSLADAINTE, wherein a corresponding polynucleotide that encodes it is in

SEQ ID NO: 4:
TCCACCAGGTCCGTGTCCTCGTCCTCCTACCGCAGGATGTTCGGCGGCCC

GGGCACCGCGAGCCGGCCGAGCTCCAGCCGGAGCTACGTGACTACGTCCA

CCCGCACCTACAGCCTGGGCAGCGCGCTGCGCCCCAGCACCAGCCGCAGC

CTCTACGCCTCGTCCCCGGGCGGCGTGTATGCCACGCGCTCCTCTGCCGT

GCGCCTGCGGAGCAGCGTGCCCGGGGTGCGGCTCCTGCAGGACTCGGTGG

ACTTCTCGCTGGCCGACGCCATCAACACCGAG

The vimentin rod domain is as follows:

(SEQ ID NO: 5)
FKNTRTNEKVELQEL NDRFANYIDK VRFLEQQNKI LLAELEQLKG

QGKSRLGDLY EEEMRELRRQ VDQLTNDKAR VEVERDNLAE

DIMRLREKLQ EEMLQREEAE NTLQSFRQDV DNASLARLDL

ERKVESLQEE IAFLKKLHEE EIQELQAQIQ EQHVQIDVDV

SKPDLTAALR DVRQQYESVA AKNLQEAEEW YKSKFADLSE

AANRNNDALR QAKQESTEYR RQVQSLTCEV DALKGTNESL

ERQMREMEEN FAVEAANYQD TIGRLQDEIQ NMKEEMARHL

REYQDLLNVK MALDIEIATY RKLLEGE, wherein a corresponding polynucleotide that encodes it is

SEQ ID NO: 6:
TTCAAGAACACCCGCACCAACGAGAAGGTGGAGCTGCAGGAGCTGAATGA

CCGCTTCGCCAACTACATCGACAAGGTGCGCTTCCTGGAGCAGCAGAATA

AGATCCTGCTGGCCGAGCTCGAGCAGCTCAAGGGCCAAGGCAAGTCGCGC

CTGGGGGACCTCTACGAGGAGGAGATGCGGGAGCTGCGCCGGCAGGTGGA

CCAGCTAACCAACGACAAAGCCCGCGTCGAGGTGGAGCGCGACAACCTGG

CCGAGGACATCATGCGCCTCCGGGAGAAATTGCAGGAGGAGATGCTTCAG

AGAGAGGAAGCCGAAAACACCCTGCAATCTTTCAGACAGGATGTTGACAA

TGCGTCTCTGGCACGTCTTGACCTTGAACGCAAAGTGGAATCTTTGCAAG

AAGAGATTGCCTTTTTGAAGAAACTCCACGAAGAGGAAATCCAGGAGCTG

CAGGCTCAGATTCAGGAACAGCATGTCCAAATCGATGTGGATGTTTCCAA

GCCTGACCTCACGGCTGCCCTGCGTGACGTACGTCAGCAATATGAAAGTG

TGGCTGCCAAGAACCTGCAGGAGGCAGAAGAATGGTACAAATCCAAGTTT

GCTGACCTCTCTGAGGCTGCCAACCGGAACAATGACGCCCTGCGCCAGGC

AAAGCAGGAGTCCACTGAGTACCGGAGACAGGTGCAGTCCCTCACCTGTG

AAGTGGATGCCCTTAAAGGAACCAATGAGTCCCTGGAACGCCAGATGCGT

GAAATGGAAGAGAACTTTGCCGTTGAAGCTGCTAACTACCAAGACACTAT

TGGCCGCCTGCAGGATGAGATTCAGAATATGAAGGAGGAAATGGCTCGTC

ACCTTCGTGAATACCAAGACCTGCTCAATGTTAAGATGGCCCTTGACATT

GAGATTGCCACCTACAGGAAGCTGCTGGAAGGCGAG

The vimentin tail domain is as follows:

(SEQ ID NO: 7)
ESRISLPLPNFSSLNLRETNLDSLPLVDTHSKRTLLIKTVETRDGQVINE

TSQHHDDLE, wherein a corresponding polynucleotide that encodes it is

SEQ ID NO: 8:
GAGAGCAGGATTTCTCTGCCTCTTCCAAACTTTTCCTCCCTGAACCTGAG

GGAAACTAATCTGGATTCACTCCCTCTGGTTGATACCCACTCAAAAGGA

CACTTCTGATTAAGACGGTTGAAACTAGAGATGGACAGGTTATCAACGAA

ACTTCTCAGCATCACGATGACCTTGAATAA

In some cases, the vimentin fragment comprises contiguous amino acids within SEQ ID NO:2, SEQ ID NO:3, SEQ ID NO:5, or SEQ ID NO:7. Such a fragment may comprise 10, 11, 12, 13, 14, 15, 16, 17, 18, 19, 20, 21, 22, 23, 24, 25, 26, 27, 28, 29, 30, 31, 37, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, or 300 amino acids of SEQ ID NO:2, SEQ ID NO:3, SEQ ID NO:5, or SEQ ID NO:7, respectively. The vimentin fragment may include an N-terminal and/or C-terminal truncation of SEQ ID NO:2, SEQ ID NO:3, SEQ ID NO:5, or SEQ ID NO:7, such as of 1, 2, 3, 4, 5, 6, 7, 8, 9, 10, 15, 20, 25, or more amino acids truncated from the N-terminal and/or C-terminal of SEQ ID NO:2, SEQ ID NO:3, SEQ ID NO:5, or SEQ ID NO:7, respectively.

As an alternative to, or in addition to, a vimentin fragment having a certain length, the fragment may comprise sequence that is at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identical to SEQ ID NO:2, SEQ ID NO:3, SEQ ID NO:5, or SEQ ID NO:7.

In particular, embodiments, the vimentin composition is formulated as a pharmaceutical composition. Pharmaceutical compositions of the present disclosure comprise an effective amount of one or more vimentin compositions dissolved or dispersed in a pharmaceutically acceptable carrier. The phrases "pharmaceutical" and "pharmacologically acceptable" and used interchangeably herein refer to molecular entities and compositions that do not produce an adverse, allergic or other untoward reaction when administered to an animal, such as, for example, a human, as appropriate, and do not interfere with the therapeutic methods of the disclosure. The preparation of a pharmaceutical composition that contains at least one vimentin composition or additional active ingredient will be known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The vimentin compositions may comprise different types of carriers depending on whether it is to be administered in solid, liquid or aerosol form, and whether it needs to be sterile for such routes of administration, such as injection. The vimentin compositions of the present disclosure can be administered intravenously, intradermally, transdermally, intrathecally, intraarterially, intraperitoneally, intranasally, intravaginally, intrarectally, topically, intramuscularly, subcutaneously, mucosally, intratumorally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The vimentin composition(s) may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present disclosure suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in practicing the methods of the present disclosure is appropriate. Examples of carriers or diluents include fats, oils, water, saline solutions, lipids, liposomes, resins, binders, fillers, alcohols, and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art. The vimentin composition may be lyophilized.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present disclosure may include the use of a pharmaceutical lipid vehicle compositions that incorporates a vimentin composition, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present disclosure.

One of ordinary skill in the art would be familiar with the range of techniques that can be employed for dispersing a composition in a lipid vehicle. For example, the vimentin composition(s) may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to the subject can be determined by physical and physiological factors such as body weight, severity of condition, the type of disease being treated, previous or concurrent therapeutic interventions, idiopathy of the subject and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% (by weight) of an active compound. In other embodiments, the active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration of the active agent, e.g., a vimentin composition according to the present disclosure, and any range derivable therein. In non-limiting examples of a derivable range from the numbers listed herein, a range of about 1 mg/kg body weight to about 100 mg/kg body weight, about 5 microgram/kg body weight to about 500 milligram/kg body weight, etc., of the active agent can be administered, based on the numbers described above.

Alimentary Compositions and Formulations

In particular embodiments of the present disclosure, the vimentin composition is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, the vimentin composition compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10% (by weight), and preferably about 1% to about 2% (by weight).

Parenteral Compositions and Formulations

In further embodiments, the vimentin composition(s) may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543, 158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (see, e.g., U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the disclosure, the active compound vimentin composition may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present disclosure may also comprise the use of a "patch". For example, the patch may supply one or more active substances at a predetermined rate and in a continuous manner over a fixed period of time.

In certain embodiments, the pharmaceutical vimentin compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (see, e.g., Takenaga et al., 1998) and lysophosphatidyl-glycerol compounds (see, e.g., U.S. Pat. No. 5,725, 871, specifically incorporated herein by reference in its entirety) are also well-known in the pharmaceutical arts. Likewise, transmucosal drug delivery in the form of a polytetrafluoroetheylene support matrix is described in, e.g., U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present disclosure for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

III. Methods of Treatment or Prevention

Embodiments of the disclosure include methods of delivering a therapeutically effective amount of one or more vimentin compositions to an individual in need thereof. In specific embodiments, the individual has or is at risk for having inflammation, such as acute inflammation. The individual may have a condition that has as a symptom and/or a mechanism an increase in adhesion of leukocytes to any tissues and/or cells, such as platelets and/or endothelial cells and/or blood vessels, for example. Embodiments of the disclosure include treatment or prevention of any medical condition in which modulation of leukocyte trafficking would be beneficial. In specific embodiments, an individual is provided a therapeutically effective amount of one or more vimentin compositions for attenuation of inflammation and/or thrombosis in an individual, including when the individual has dysregulation of physiological processes following which leads to inflammation and/or thrombosis.

In specific embodiments, the medical condition treated or prevented with vimentin comprises acute lung injury, primary and secondary acute lung injury (e.g., secondary lung injury after sepsis or blood transfusion), ischemia/reperfusion injury (including but not limited to stroke and myocardial ischemia), trauma, sepsis (acute infection), pancreatitis, drug-induced organ injury (acetaminophen-induced lung injury, for example), extracorporeal life support(e.g., extracorporeal membrane oxygenation, cardiopulmonary bypass, ventricular assist devices, dialysis or other blood purification systems such as plasma exchange or extracorporeal liver support devices), hyper-inflammatory syndromes (e.g., autoimmune disorders and hemophagocytic lymphohistiocytosis), myocarditis, or a combination thereof.

In particular embodiments, chronic inflammation is not treated with methods of the disclosure. In specific embodiments, a medical condition treated or prevented with vimentin is one in which neutrophils play a role, such as neutrophil adhesion to platelets. In some cases, the vimentin treats or prevents the medical condition in the individual by decreasing leukocyte adhesion to platelets, neutrophil adhesion to platelets, neutrophil adhesion to endothelial cells, and/or neutrophil adhesion to P-selectin, for example.

Embodiments of the disclosure include methods that prevent the development of ALI or the progression from ALI to ARDS. In specific embodiments, methods of the disclosure include those that prevent worsening of respiratory function (e.g. the development of hypoxemia and/or hypercapnia) the need for intubation of an individual or reduce complications associated with mechanical ventilation (e.g., ventilator associated lung injury, pneumothorax, refractory hypoxemia, death). In some cases, once an individual appears to be at risk for developing ALI, ARDS, or requiring intubation, an individual is given an effective amount of one or more vimentin compositions as part of their care.

In specific cases, delivery of vimentin to an individual blocks the pathologic inflammation that leads to ALI/ARDS. In particular cases, vimentin blocks leukocytes from binding to platelets and blood vessels, thereby reducing damage from otherwise healthy sites. Specific embodiments of the disclosure include methods in which a vimentin composition targets P-selectin on platelets and/or blood vessels. In particular, vimentin decreases inflammation by inhibiting leukocyte adhesion to platelets and endothelium via blocking P-selectin-PSGL-1 interactions. In particular cases, the rod domain of vimentin preferentially binds to P-selectin instead of PSGL-1, although in alternative embodiments in certain cases vimentin binds to PSGL-1 for a therapeutic outcome.

In certain embodiments, vimentin composition(s) are used for the treatment or prevention of sterile inflammation (an event triggered by physical, chemical or metabolic insults that cause cell stress and hence stress responses). In specific embodiments, the sterile inflammation is associated with trauma, secondary ARDS, liver injury, ischemia/reperfusion (e.g., stroke and myocardial infarction) or artificial surfaces, such as those related to extracorporeal devices (e.g. cardiopulmonary bypass, ventricular assist devices, dialysis machines (hemodialysis and continuous renal replacement therapy), extracorporeal liver support machines, blood tubing, catheters, filters, centrifugal or roller pumps, oxygenators).

Although in some cases the vimentin composition is provided as a sole therapy for the individual, in some cases the individual is provided a second therapy. The second therapy may be of any kind, but in specific cases the second therapy is a corticosteroid, antibodies, GSnP-6, sialyl Lewis X analog, anti-proliferatives, calcineurin inhibitors, anti-signaling compounds, or a combination thereof. Vimentin composition may also be second therapy to attenuate inflammation until the primary process is resolved (e.g., resolution of infection, discontinuation or removal of artificial surfaces, time after reperfusion injury).

In particular embodiments, an individual that is at risk for acute inflammation or that is known to have acute inflammation is provided a therapeutically effective amount of one or more vimentin compositions. In some cases, the individual has been diagnosed with acute inflammation, ALI, or ARDS, for example. Stimuli for acute inflammation include infections (for example, bacterial, viral, fungal, parasitic) and microbial toxins; tissue necrosis, such as ischemia, trauma, physical or chemical injury (e.g., thermal injury; irradiation; some environmental chemicals); foreign bodies (splinters, dirt, sutures); or immune reactions (also referred to as hypersensitivity reactions), and an individual exposed to (or that will be exposed to) one or more of these may be provided an effective amount of one or more vimentin compositions.

In some embodiments, a medical condition is treated or prevented with a vimentin composition that is delivered to the individual multiple times, such as once a day, more than once a day, one a week, more than once a week, once a month, more than once a month, once a year, or more than once a year. The multiple treatments may or may not have the same formulations and/or routes of administration(s). Any administration may be as a continuous infusion.

The provider skilled in the art of medical care and decision may determine an appropriate end-point for vimentin composition therapy based on the specific disease process and clinical course of the patient or individual.

IV. Kits

Any of the vimentin compositions described herein may be part of a kit. The kits may comprise a suitably aliquoted vimentin composition of the present disclosure, and the component(s) of the kits may be packaged either in aqueous media or in lyophilized form. The container of the kits will generally include at least one vial, test tube, flask, bottle, syringe or other container, into which a component may be placed, and preferably, suitably aliquoted. Where there is more than one component in the kit, the kit also will generally contain a second, third or other additional container into which the additional component(s) may be separately placed. However, various combinations of components may be comprised in a vial. The kits of the present disclosure also will typically include container for holding the vimentin composition and any other reagent containers in close confinement for commercial sale.

When the components of the kit are provided in one and/or more liquid solutions, the liquid solution is an aqueous solution, with a sterile aqueous solution being contemplated. The compositions may also be formulated into a syringeable composition. In which case, the container may itself be a syringe, pipette, and/or other such like apparatus, from which the formulation may be applied to a particular area of the body, injected into an individual, and/or even applied to and/or mixed with the other components of the kit. However, the component(s) of the kit may be provided as dried powder(s). When reagents and/or components are provided as a dry powder, the powder can be reconstituted by the addition of a suitable solvent. It is envisioned that the solvent may also be provided in another container.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Soluble Vimentin to Block Inflammation in Acute Lung Injury

Microvascular inflammation is central to the pathophysiology of a number of serious disease states, including trauma, reperfusion injury, acute lung injury, and sepsis (Zarbock et al., 2006; Sun et al., 2012; Murohara et al., 1996; Lerman et al., 2014), and culminates in the recruitment and transendothelial migration of neutrophils in post-capillary venules (Zarbock et al., 2007; Burns et al., 1997). The earliest step of this process is the capture of rolling of leukocytes, primarily neutrophils, onto the microvascular endothelium. These early steps are mediated through cell surface adhesion molecules on the leukocytes to counter-receptors on both platelets and endothelium (Diacovo et al., 1996; Lam et al., 2011; Konstantopoulos et al., 1998; Jones et al., 1993; Moore et al., 1992; Smith et al., 1988). Normally, inflammation is important in the maintenance of health, such as in infection and wound healing. However, inflammation can also be pathologic, leading to tissue injury and organ dysfunction both in the directly injured, as in ischemia/reperfusion injury (Murohara et al., 1996; Fernandes et al., 2003), as well as distant sites, such as in extra-pulmonary (secondary) ALI/ARDS from sepsis (Asaduzzaman et al., 2009; Xiao et al., 2006; Craig et al., 2009) (reviewed in (Iskander et al., 2013)), trauma (Abrams et al., 2013), blood transfusion (Fortenberry et al., 1996), and inflammation from extracorporeal life support devices (Fortenberry et al., 1996; McIlwain et al., 2010), for example. Blocking these interactions may have a beneficial role in decreasing pathologic inflammation in these and other disease states.

Platelets have increasingly been shown to play an important role in pathologic inflammation (reviewed in (Lam et al., 2015)), including the development of acute lung injury (Asaduzzaman et al., 2009; Caudriller et al., 2012); depleting platelets prior to injury attenuates the lung injury and improves mortality in murine models of acid-induced lung injury and bacterial peritonitis-induced lung injury. This is most likely through platelets' ability to enhance capture of leukocytes onto inflamed endothelium (Fernandes et al., 2003; Kuijper et al., 1997) as well as enhancing neutrophil transendothelial migration, as previously described (Lam et al., 2011). Blocking these cell-cell interactions would improve the outcome for patients with pathologic inflammation, in particular embodiments.

One way to block these interactions is through using soluble recombinant human vimentin (srhVim). Vimentin is an intracellular, type 3 intermediate filament protein that is important for maintaining the cytoskeleton and for intracellular transport. It is primarily found as helical dimers and tetramers and has three main domains: the head, rod, and tail (Ivaska et al., 2007). Although its original description has been as an intracellular protein, increasing data suggest that vimentin is also expressed on the cell surface of platelets (Da et al., 2014; Podor et al., 2001), endothelial cells (Pall et al., 2011), as well as secreted by macrophages (Mor-Vaknin et al., 2003). The role of vimentin during inflammation has been unclear, with studies suggesting that vimentin may be important for lymphocyte trafficking (Nieminen et al., 2006) versus others that suggest vimentin inhibits inflammation (Mor-Vaknin et al., 2013). Recently, vimentin has been described as a lectin-binding protein (Ise et al., 2010), suggesting a potential use in blocking leukocyte-platelet-endothelial interactions. As shown herein in specific embodiments, srhVim blocks neutrophil adhesion to platelets and endothelium and decreases leukocytic infiltration into lungs of endotoxemic mice.

Currently, treatments used to improve outcomes in ARDS, such as corticosteroids, have many undesirable side effects and have not been effective (Rhen and Cidlowski, 2005). Embodiments of this disclosure encompass srhVim for reducing pulmonary inflammation and improvement of endotoxin-induced lung injury. Embodiments of the disclosure include treatment to reduce the morbidity and mortality from ALI/ARDS. Furthermore, becaues the mechanism of action of srhVim is through blocking leukocyte adhesion, certain embodiments encompass srhVim and its components for reduction of inflammation and improvement in other inflammatory diseases, such as ischemia/reperfusion injury, trauma, and inflammation from extracorporeal life support devices, for example.

In specific embodiments, one can characterize smaller fragments of srhVim in order to identify one or more active motifs that block P-selectin-PSGL-1 interactions. One can screen candidate protein fragment(s) using in vitro leukocyte adhesion assays as well as measuring binding kinetics to P-selectin and also can test in vivo. One can study the efficacy of vimentin in preventing or attenuating ARDS, for example using two porcine models of secondary ARDS: endotoxemia and MRSA bacteremia. The benefit of the porcine models for ARDS is that it more closely approximates the pathophysiologic changes seen in humans with ARDS, as opposed to murine models (Matute-Bello et al., 2008) and have advantages over rodent models in testing new pharmaceutical therapies (Bode et al., 2010; Forster et al., 2010). One can utilize piglets, weighing approximately 10 kg, in order to recapitulate children with acute lung injury and ARDS. One can determine whether srhVim reduces acute lung injury in septic piglets using endotoxemia and MRSA bacteremia as two separate models. One can measure the degree of leukocytic infiltration in the lungs using histologic preparations and measure serial blood gases to determine lung function. Additionally, one can test positively screened candidate proteins for their effects on mitigating the development of ALI and ARDS. One can also study the safety profile of short term use. One can evaluate for antibody production against srhVim as well as the effects on organ function, measuring blood chemistries, as well as evaluating for potential deposition of srhVim into tissue.

Figure 2:
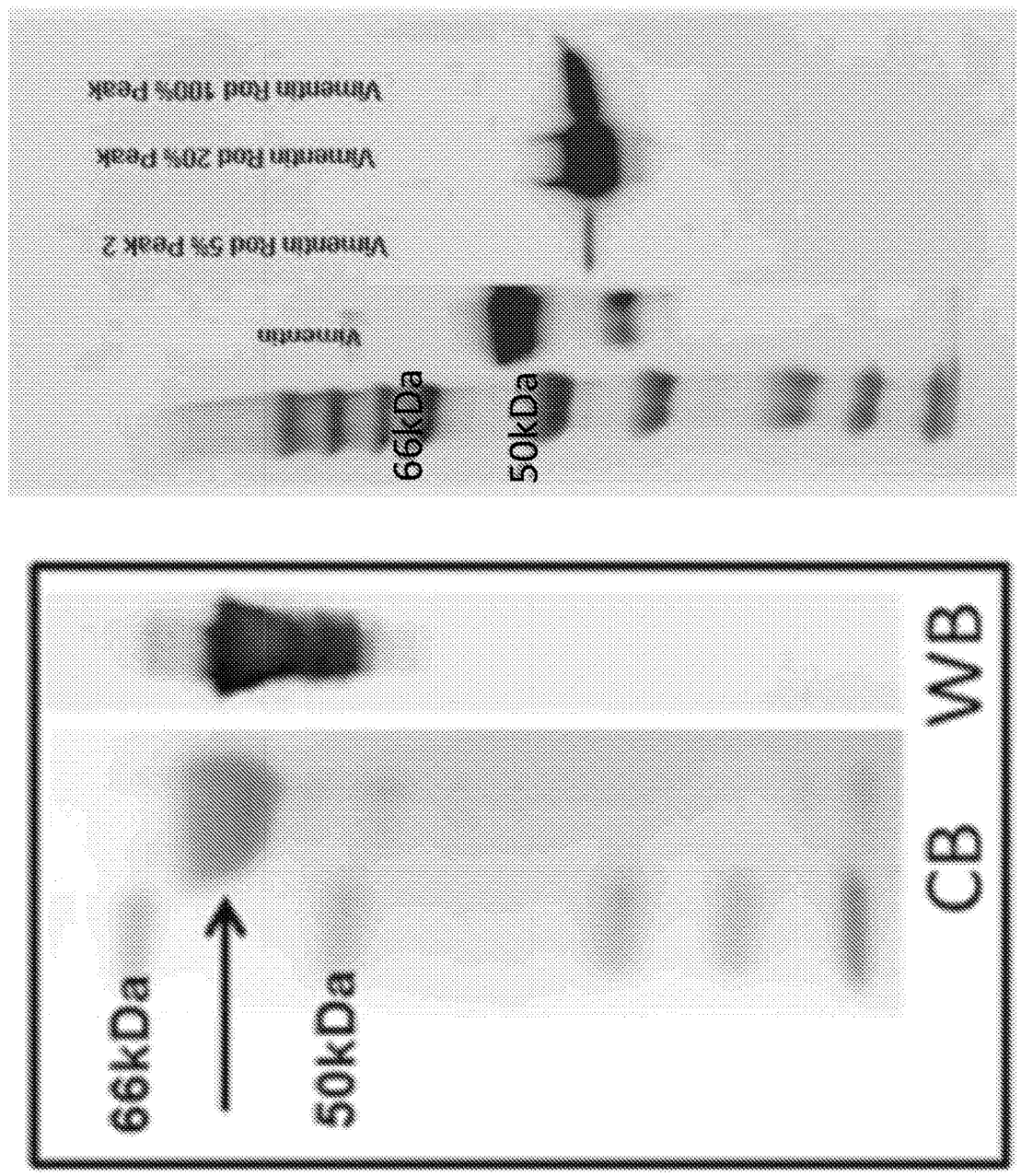
FIG. 2 (Left) SDS-Page of (arrow) srhVim under reduced conditions and visualized with Coomassie Blue (CB) and Western blot (WB) using anti-vimentin antibodies. (Right) WB of Vimentin as well as the rod domain.

This example provides the following:

(A) Purification of soluble recombinant human vimentin and the rod domain (FIG. 2): Polynucleotides encoding full length vimentin and its rod domain (amino acids 96-407) were separately incorporated into pET30 and transformed into Escherichia coli for protein purification using a $Ni^{2+}$ column. Western blot (WB) and Coomassie blue staining (CB) confirmed the presence of vimentin (FIG. 2).

Figure 3A:
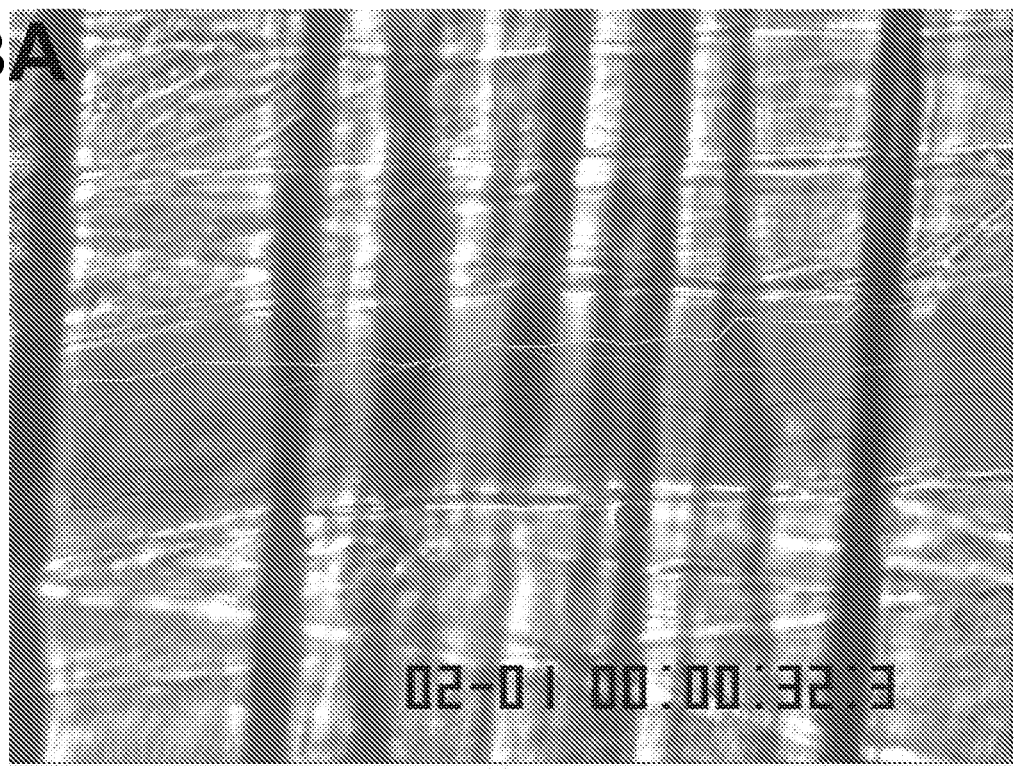
FIGS. 3A and 3B.
Figure 3B:
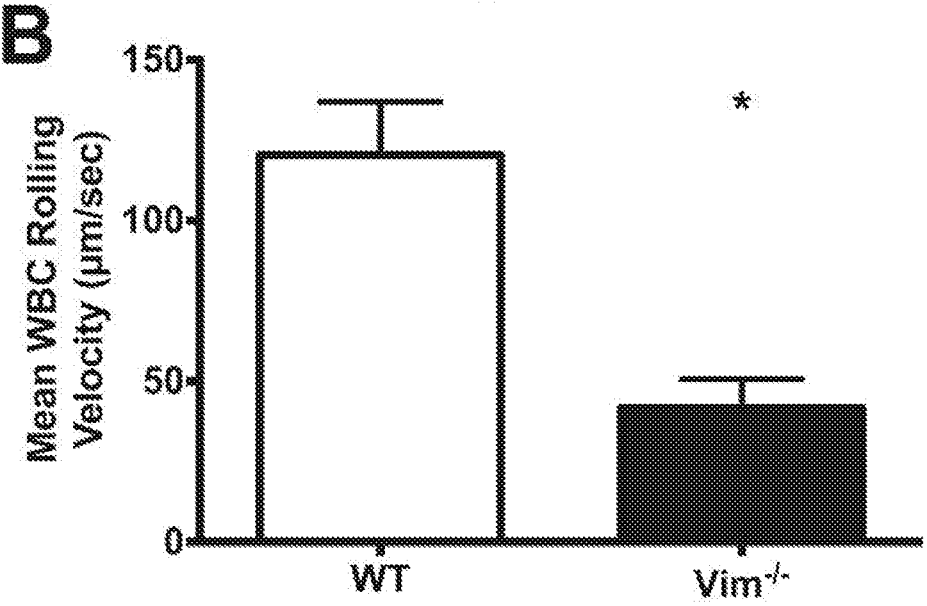

(B) Leukocytes (WBC) in vimentin knockout ($Vim^{-/-}$) mice have slower rolling velocities in venules than wildtype mice (FIG. 3): Using intravital microscopy of the cremaster muscle vascular bed, a blinded investigator calculated the average rolling velocity of WBC in post-capillary venules. WBC velocity was significantly slower in $Vim^{-/-}$ mice compared to WT controls. This is despite similar venular shear rates between $Vim^{-/-}$ and WT mice (452±53 vs. 423±36 sec-1, n=4 mice/group, p>0.05).

(C) srhVim decreases human leukocyte adhesion to fibrinogen monolayers (FIG. 4): Based on intravital observations in mice, the effect was studied of srhVim on WBC adhesion under flow over fibrinogen monolayers using the BioFlux microfluidic parallel plate flow system (Fluxion Biosciences). This system allows for multiple flow adhesion assays (up to 24 conditions) to be performed and evaluated simultaneously while precisely controlling shear stress. Citrated whole blood was collected from healthy adult subjects after consent was obtained. WBC and platelets were labeled through the addition of mepacrine, which labels granules without affecting leukocyte or platelet function (22). The mepacrine-labeled blood was then perfused through the system at 2 dyn/cm$^2$, representing the post-capillary venule shear stress at which WBC adhere to vascular endothelium (reviewed in (Lam et al., 2013)). There were no differences in platelet adhesion to the fibrinogen surface based on fluorescence intensity. srhVim 50 µg/mL significantly decreased the number of adhered WBC flowing over fibrinogen monolayers (FIG. 4B).

(D) srhVim decreases human neutrophil (PMN) adhesion to platelet monolayers in a dose-dependent fashion (FIG. 5): To determine whether observations that srhVim decreases WBC adhesion to fibrinogen were because of WBC-fibrinogen interactions (Altieri et al., 1990) or WBC-platelet interactions (Diacovo et al., 1996; Lam et al., 2011), the inventors perfused (2 dyn/cm$^2$) isolated human PMN (Lam et al., 2011) over microfluidic channels coated with fibrinogen (100 m/mL), platelets ($4 \times 10^8$/mL), or no coating (glass). Isolated PMN did not adhere to fibrinogen-coated channels, with or without srhVim. srhVim also had no effect on PMN adhesion to glass. However, the presence of srhVim significantly decreased PMN adhesion to platelet monolayers. srhVim decreased PMN adhesion to platelets a dose-dependent fashion.

(E) srhVim decreases human neutrophil adhesion to IL-1β stimulated human umbilical vein endothelial cells (HUVEC): To determine whether srhVim also inhibits PMN adhesion to endothelial cells, HUVEC were cultured on fibronectin-coated microfluidic channels. Once the HUVEC reached 100% confluence, isolated PMN were perfused in the presence of srhVim (40 µg/mL) or vehicle control. The presence of srhVim significantly decreased the number of adherent PMN to HUVEC monolayers by ~57% (121.7±62.6 vs. 279.2±89.2 PMN/field, n=6 paired subjects, p<0.05).

(F) srhVim blocks PMN adhesion by preferentially binding to P-selectin in order to block P-selectin-P-selectin glycoprotein ligand-1 (PSGL-1) interactions (FIG. 6): because of the multiple adhesive interactions between PMN and platelets, the cell adhesion molecules were further considered. Isolated PMN were infused over channels coated with P-selectin/Fc chimeric protein (10 µg/mL) in the presence of various concentrations of srhVim. Similar to observations with platelet monolayers, the presence of srhVim decreased PMN adhesion to P-selectin/Fc monolayers in a dose-dependent fashion.

The observations in these experiments, in certain embodiments, are attributed to srhVim either affecting P-selectin, PSGL-1, or both. ELISA was performed by coating 96-well plates with either PSGL-1/Fc protein (10 µg/mL), P-selectin/Fc protein (10 µg/mL), or BSA (10 µg/mL) and adding various concentrations of srhVim to each well. Detection was through anti-His/HRP antibodies. Increasing amounts of srhVim bound to P-selectin/Fc protein and reached saturation at 20 µg/mL. There was no binding of srhVim to PSGL-1/Fc (FIG. 6B). Finally, the binding kinetics were evaluated of both the full and rod domain of vimentin to P-sel/Fc protein (compared to IgG control) using surface plasmon resonance (BIACore) and a KD of ~67 nM was measured for full length vimentin and ~125 nM for the rod domain for binding to immobilized P-sel/Fc (FIG. 6C)

(G) Mice exposed to endotoxin (LPS) have improved activity when treated with srhVim and appear to have less leukocytic infiltration into the lungs (FIG. 7): To determine whether srhVim had any clinical effects, mice were treated with a sub-lethal dose of endotoxin (15 mg/kg i.p.) to induce a secondary acute lung injury. Mice were given srhVim (3 mg/kg) or vehicle control simultaneously. Blinded investigators evaluated the mice every 12 hours, using a validated murine scoring system (M-CASS) (42). Mice receiving srhVim had improved activity 24 hours after LPS injection (1.9±0.2 vs 2.5±0.2; 4-point scale where lower is better; srhVim and control, respectively; n=10/grp, p<0.05). Preliminary autopsies at 96 hours suggest decreased leukocytic infiltration into the lungs in mice receiving srhVim (FIG. 7).

(H) Piglets exposed to endotoxin (LPS) and MRSA bacteremia develop leukocytic infiltrates into the lungs (FIG. 8): Initial experiments in endotoxemic piglets (<10 kg; 10 µg/kg) show increased interstitial thickening and neutrophilic infiltration into the lungs (FIGS. 8A & 8B). To evaluate an MRSA bacteremia model of sepsis (43), MRSA $1 \times 10^9$ CFU/kg (strain USA 300, TCH 1516), was injected intravenously into piglets. Piglets were continuously monitored for 70 hours prior to euthanasia. Piglets receiving MRSA had greater leukocytic infiltrate into the lungs than saline control (FIGS. 8C & 8D).

Thus, the initial data of these studies indicates at least the following: 1) A soluble form of recombinant human vimentin and its rod domain were generated; 2) Leukocyte rolling velocity in mice lacking vimentin is slower than in control mice; 3) srhVim decreases WBC binding to platelets, endothelial cells, and recombinant P-selectin monolayers; 4) srhVim and its rod domain preferentially bind to P-selectin; 5) Endotoxemic mice receiving srhVim have improved activity and have decreased leukocytic infiltration into the lungs; and 6) Piglets develop leukocytic infiltration into the lungs in two different models of experimental sepsis: endotoxemia and MRSA bacteremia.

Based on the above-referenced data, one can identify at least one active domain within vimentin that blocks P-selectin-PSGL-1 interactions and can study the safety and efficacy of srhVim in preventing and treating acute lung injury and ARDS in a large animal model of experimental sepsis.

In particular, one can identify the active motif and binding kinetics of vimentin-P-selectin interactions. In specific embodiments, at least one active binding motif that accounts for vimentin-P-selectin interactions is within the rod domain. In specific cases, biophysical interactions between vimentin and P-selectin are characterized. One can identify a more specific, and possibly less immunogenic, peptide to use to attenuate pathologic inflammation as we had shown with full-length vimentin. One can further define the biophysical properties of vimentin-P-selectin interactions in model as well as in naturally occurring extracellular vimentin. Finally, data from these experiments allows determination of the pharmacokinetics of srhVim using standard methods in the art.

Experiment 1.1: Develop and test subcomponents of srhVim on blocking leukocyte adhesion. Based on the initial data, the srhVim binding to P-selectin is in the rod domain, in specific embodiments. However, one can also test the head or tail domains (or overlapping regions of any one or more domains, such as spanning between head-rod and/or rod-tail) as these may also have affinity for P-selectin. Therefore, one can generate His-tagged head and tail domains. One can use a similar technique as described above, using pET30 to insert the gene(s) into E. coli. Supernatant from transformed bacteria is collected and affinity purified via a Ni$^{2+}$ column to bind the histidine tag. Purified protein is serially dialyzed against phosphate buffer for stability. In addition to the main domains, one can generate smaller regions of the rod domain using 10-20 amino acid segments. One can then test these smaller fragments using the in vitro system of leukocyte rolling and adhesion over platelets, P-selectin, and activated endothelium as described above. Domains and fragments that block leukocyte adhesion to platelets, P-selectin, and activated endothelium are tested for binding kinetics, as described below.

Experiment 1.2: Evaluate the binding kinetics of P, E, and L-selectin to different components of vimentin. Based on preliminary data with full-length and rod-domain vimentin (FIG. 6), vimentin binds to P-selectin, most likely in the rod domain, in at least some embodiments. In this proposal, one can use surface plasmon resonance (SPR; Biacore) to determine the KD of srhVim and its main domains (head, tail, and rod domains) to P-, E-, and L-selectin, comparing them to PSGL-1, since they are also important cell adhesion molecules that participate in leukocyte-endothelial and leukocyte-leukocyte interactions. In addition to testing the main domains, one can also test the binding kinetics of the smaller fragments that block leukocyte adhesion. One can then select the components with the strongest KD to P-selectin to utilize in the porcine models of experimental sepsis (see below).

Experiment 1.3. Characterize the structure of srhVim and its components in the presence and absence of P-selectin using circular dichroism (CD): One can use circular dichroism to characterize the secondary structure of srhVim and P-selectin in solution and characterize whether they change in combination. A limitation of this method is that it does not provide information of structure in the solid state; however, in specific embodiments the use of srhVim is in the liquid state (in plasma).

In alternative embodiments, one can assess modifications to the rod domain to adjust its KD in order to tailor its effect on neutrophil adhesion.

In an embodiment, one can evaluate the efficacy and safety of srhVim to attenuate acute lung injury in two pre-clinical, porcine models of experimental sepsis: endotoxemia and methicillin resistant *Staphylococcus aureus* (MRSA) bacteremia. Based on in vitro and in vivo murine data, srhVim has a protective effect against the development of endotoxin-induced acute lung injury and ARDS. One can study two different models of experimental sepsis to determine whether the type of inflammation (sterile [endotoxemia] versus infectious [MRSA bacteremia]) affects the efficacy of srhVim on preventing or attenuating ARDS. One can also determine whether both acute administration of srhVim results in antibody production and/or end organ injury.

In specific embodiments, one can evaluate the efficacy of srhVim and its components on attenuating acute lung injury in two porcine models of experimental sepsis. In particular embodiments, srhVim will reduce acute lung injury in piglets, such as by decreasing leukocytic infiltration into the lungs after induction of experimental sepsis.

Experiment 2.1.1: Evaluation of the effect of srhVim on decreasing leukocytic infiltration into the lungs and improving gas exchange in a model of endotoxin-induced acute lung injury in piglets. Based on experiments described above, piglets are exposed to endotoxin (LPS; 50 mcg/kg/h over 2 hours) and treated with srhVim. Endotoxin or saline control (sham) may be infused intravenously, followed by either srhVim (3 mg/kg) or vehicle control 1 hour later. Based on observations in mice, 4 piglets per group (Sham/Vehicle, Sham/srhVim, LPS/Vehicle, and LPS/srhVim) are used to detect a reduction in leukocytes in the lung by 50% (power 0.8, $\alpha=0.05$).

After inducing a surgical plane of anesthesia, piglets would have jugular venous and carotid artery catheters inserted for infusion and blood sampling, respectfully. Additionally, an intra-arterial femoral catheter is placed for continuous pulse, blood pressure, and temperature monitoring via telemetry. After the piglets recover from surgery, they would receive either intravenous LPS (50 mcg/kg over 2 hours) or saline control (46). One hour after completion of LPS infusion, the animals receive either intravenous srhVim (3 mg/kg) or vehicle control. Animals are then continuously monitored for 24 hours, with blood collected at baseline (before LPS/Sham infusion) and every 6 hours thereafter for arterial blood gases, complete blood counts, disseminated intravascular coagulation panels, serum chemistries, and additional plasma may be collected and frozen for further studies. Piglets re allowed to eat ad libitum and are also given dextrose-containing intravenous fluids for hydration and to prevent hypoglycemia. At the end of 24 hours, or if the animals are moribund, the animals may be euthanized and organs collected (formalin and frozen sections) for histology to quantify leukocytic infiltration using a combination of hematoxylin and eosin and anti-leukocyte antibody staining, for example.

Experiment 2.1.2: Evaluation of the effect of srhVim on decreasing leukocytic infiltration into the lungs and improving gas exchange in a model of MRSA bacteremia (USA 300, TCH 1516 Strain) induced acute lung injury in piglets. Based on studies described above, one can expose piglets to MRSA (USA 300, TCH 1516 Strain; $1 \times 10^9$ CFU/kg), followed by either srhVim (3 mg/kg) or vehicle control 1 hour later. Based on observations in mice, one can utilize 4 piglets per group (Sham/Vehicle, Sham/srhVim, MRSA/Vehicle, and MRSA/srhVim) to detect a reduction in leukocytes in the lung by 50% (power 0.8, $\alpha=0.05$).

Preparation of piglets may be similar to that described above. After the piglets recover from the placement of jugular, carotid, and femoral artery catheters, they can receive either intravenous MRSA or saline control (Soerensen et al., 2013). One hour after completion of MRSA infusion, the animals can receive either intravenous srhVim (3 mg/kg) or vehicle control. Animals are then continuously monitored for 70 hours. Piglets are allowed to eat ad libitum and are also given dextrose-containing intravenous fluids for hydration and to prevent hypoglycemia. Blood is collected at baseline (before MRSA/Sham infusion) and then at 24, 36, 48, 60, and 70 hours thereafter for complete blood counts, disseminated intravascular coagulation panels, serum chemistries, and additional plasma will be collected and frozen for further studies. Arterial blood gases are measured at baseline and 70 hours (or if moribund). At the end of 70 hours, or if the animals are moribund, the animals are euthanized and organs collected (formalin and frozen sections), for example for histology to quantify leukocytic infiltration using a combination of hematoxylin and eosin and anti-leukocyte antibody staining.

In particular embodiments, srhVim decreases acute lung injury after both endotoxemia and MRSA bacteremia, with improved gas exchange and less leukocytic infiltration of the lungs in piglets receiving srhVim. Further studies may include (1) dose titration of srhVim to optimize dosing and (2) adjusting the timing between injury and srhVim to determine whether srhVim is still efficacious after a delay in treatment. Finally, aside from testing full-length srhVim, candidate proteins are tested for their ability to attenuate ALI/ARDS.

Evaluation of the efficacy of srhVim and its components on attenuating acute lung injury in two porcine models of experimental sepsis: In specific embodiments, srhVim has a tolerable safety profile, including no immunogenicity, minimal effect on organ function and deposition, and minimal effect on coagulation and thrombosis.

Evaluation of the development of antibodies to srhVim: Because of use of a protein, there is a risk of antibody development. Therefore, one can inject a separate set of piglets with different doses of srhVim (0, 1.5, 3, and 6 mg/kg) and collect serum weekly for 8 weeks to evaluate for the development of anti-vimentin antibodies. Collected serum is added to vimentin-coated plates to capture anti-vimentin antibodies, followed by detection using anti-pig IgG/HRP and anti-pig IgM/HRP antibodies. Levels are compared to baseline. Additionally, organs are prepared for immunofluorescence to evaluate for immune complex deposition using anti-His and anti-pig IgG antibodies.

Evaluation of the effect of srhVim on organ function and organ deposition. These experiments may be simultaneous with the experiments described above. Plasma and serum collected from these experiments are analyzed for evidence of end-organ dysfunction (e.g. chemistries, liver panel, coagulation profiles, complete blood counts). Organs are collected for histology, staining for srhVim deposition using anti-His/HRP antibodies. Additional histologic studies evaluate for microvascular thrombosis, since vimentin interacts with von Willebrand factor (VWF) under high shear (Da et al., 2014). In addition to hematoxylin and eosin staining, one can stain slides with anti-His, anti-VWF, anti-CD31 (PECAM; endothelial marker), anti-fibrin(ogen), and anti-CD41 (platelet marker) to evaluate for thrombosis and to determine their composition, if they occur.

Evaluation of the effect of srhVim on the clearance of bacteremia. Because srhVim blocks leukocyte adhesion to platelets and endothelium, there is a risk of decreased clearance of bacteria from tissue. Concurrently, one can measure blood cultures of piglets exposed to MRSA bacteremia to determine whether treatment with srhVim inhibits clearance of bacteria. In addition, one perform Gram staining of formalin-fixed, paraffin embedded tissue to evaluate for microabscesses.

Example 2

Example of Synthetic Vimentin Production

One embodiment of producing synthetic vimentin is as described. Inclusion bodies come from lysed *E. coli* were solubilized with GHCl. After centrifugation, the solubilized pellet (GHCl-Vim) for 30 min at full speed (20,000 rpm), the supernatant is filtered through 0.45 um and slowly diluted 40× in cold buffer—25mM Tris-Cl, 1.0 M NaCl, 0.5% Tween-20, pH-7.4 (this buffer is prepared the day before and stored in the cold room). Equilibrate the cold Nickel column with Buffer A (25 mM Tris-Cl, 1.0 M NaCl, 0.5% Tween-20, pH-7.4). If the diluted solution remains crystal clear, then it is suitable for the Nickel column. Wash the column with Buffer A until OD is near baseline. Elute the first peak with 5% Imidazole (Buffer B-500 mM Imidazole, 25 mM Tris-Cl, 1.0 M, NaCl, 0.5% Tween-20, pH-7.4), and continue until OD reach back the baseline. Elute the vimentin protein with 40% Imidazole. The collected peak is then dialyzed against cold 10 mM $Na_2PO_4$, pH-8.0 overnight. Filter the solution through 0.2 uM, and check concentration at OD of 280 nM using $\varepsilon=24,000$ $cm^{-1}M^{-1}$ Mol Weight=55,091 g/moL.

Example 3

Vimentin Administration to an Individual

Vimentin, including recombinant vimentin, and/or its fragments or derivatives thereof, may be utilized in mammalian individuals (such as human subjects or patients), and such administration attenuates the development or progression of acute lung injury (as one example of pathologic inflammation), in particular embodiments. As one example only, an individual that presents to a medical emergency facility (such as an emergency room) with risk factors for acute lung injury (including but not limited to sepsis, trauma, blood product transfusion, pancreatitis, or a combination thereof) would be given a dose of recombinant vimentin and/or its fragments or derivatives thereof (such as intravenously) in addition to other supportive care (such as antibiotics, fluids, oxygen, etc.). The individual's lung function may be monitored using standard clinical variables (such as oxygen saturation, respiratory rate, blood gas measurements, physical examination findings, diagnostic imaging, etc., or a combination thereof). Multiple doses may be utilized if the individual has ongoing worsening of lung function. As the individual improves by means of requiring de-escalation of medical support, the vimentin and/or its fragments or derivatives thereof may be discontinued. Endpoints of successful intervention include stable or improving lung function, such as demonstrated by physical examination and respiratory rate normalization, improving pAO2/FiO2 ratio (P/F ratio), normalization of $pCO_2$, preventing need for intubation and mechanical ventilation, (for those mechanically ventilated) decreased number of ventilator days, decreased hospital length of stay, decreased intensive care unit length of stay, or a combination thereof. Doses and/or routes may be varied.

Example 4

Recombinant Human Vimentin Binds to P-Selectin and Blocks Neutrophil Capture and Rolling on Platelets and Endothelium Introduction Leukocyte (WBC) interaction and adhesion to platelets and vascular endothelium plays an integral role in the initiation of inflammation. These early steps are mediated through cell surface adhesion molecules on the leukocytes (e.g., P-selectin glycoprotein ligand-1 [PSGL-1] and CD11b/18 [Mac-1]) to counter-receptors on platelets and endothelium (e.g. P-selectin (P-sel), glycoprotein 1bα [GP1bα], E-selectin, and ICAM-1) (Diacovo, et al., 1996; Jones, et al., 1993; Konstantopoulos, et al., 1998; Lam, et al., 2011; Moore, et al., 1992; Smith, et al., 1988). In most cases, the presence of inflammation plays an important role in the maintenance of health, such as in infection (Lerman, et al., 2014) and wound healing (Li, et al., 2006). However, in pathologic inflammation, these processes may lead to more tissue injury and organ dysfunction, such as in acute lung injury (Zarbock, et al., 2006; Asaduzzaman, et al., 2009), ischemia/reperfusion injury (Fernandes, et al., 2003; Murohara, et al., 1996), and inflammation from extracorporeal life support devices (Fortenberry, et al., 1996; Timpa, et al., 2010). Therefore, in particular embodiments of the disclosure blocking these interactions has a beneficial role in decreasing pathologic inflammation in specific disease states.

One way to block leukocyte interaction with platelets and endothelium is through inhibiting the binding of leukocyte surface adhesion molecules to those on platelets and endothelium. There is an important role of PSGL-1-P-selectin interactions on leukocyte adhesion to (Fernandes, et al., 2003) and transmigration across (Lam, et al., 2011) vascular endothelium. In a murine model of experimental acute lung injury, blocking P-selectin using a monoclonal antibody improved oxygenation and decreased leukocytic infiltration into the lungs (Zarbock, et al., 2006).

Vimentin is an intracellular, type 3 intermediate filament protein that is important for maintaining the cytoskeleton as well as intracellular transport. It is highly conserved, with ~96% homology between humans and mice and, in its native state, it is mainly found as helical dimers and tetramers (Chernyatina, et al., 2012). Vimentin is primarily located within mesenchymal cells but recently, it has also been reported on the surface of cells (Da, et al., 2014) as well as secreted into the plasma (Mor-Vaknin, et al., 2003). Previous reports on the role of vimentin in inflammation have been conflicted, with reports of vimentin knockout mice having both increased phagocytic capabilities (Mor-Vaknin, et al., 2013), as well as decreased lymphocyte adhesion and transmigration across endothelial cells (Nieminen, et al., 2006). This discrepancy may be because of the differential functions of intracellular and extracellular vimentin (Ivaska, et al., 2007).

Although the exact role of vimentin in inflammation is complex, vimentin has recently been reported to bind to N-acetylglucosamine(Ise, et al., 2010), a moiety that is present on PSGL-1 on leukocytes (McEver, et al., 1997; Wilkins, et al., 1996). In addition, soluble CD44, the soluble form of E-selectin ligand normally found on neutrophils (Katayama, et al., 2005), was recently reported to bind to vimentin (Pall, et al., 2011). In addition to E-selectin, CD44 variants have been reported to interact with P- and L-selectin (Hanley, et al., 2006). Based on these data, it was considered that recombinant human vimentin (rhVim) inhibits leukocyte adhesion to platelets and endothelium through blocking interactions between the selectins and their ligands, in specific embodiments.

Examples of Materials and Methods

Ethics statement—Human and animal subject research were approved by the Institutional Review Boards and Institutional Animal Care and Use Committees at Baylor College of Medicine and Michael E. DeBakey Veterans Affairs Medical Center.

Materials—*Escherichia coli* (Strain M15) was purchased from Qiagen. Horseradish peroxidase (HRP)-conjugated anti-polyhistidine antibody, 1× protease inhibitor, bovine serum albumin (BSA), tetramethylbenzidine, and mepacrine were purchased from Sigma-Aldrich. Dulbecco's phosphate buffered saline (DPBS) was purchased from Gibco. Recombinant human interleukin-1β (rhIL-1β), P-selectin/Fc, E-selectin/Fc, and PSGL-1/Fc were purchased from R & D Systems. Human IgG was purchased from Pierce. Sheep anti-vimentin antibody was purchased from Affinity Biologicals. Rabbit anti-vimentin (H-84; N-terminus), rabbit anti-vimentin (C-20; C-terminus), and mouse anti-vimentin (E-5; C-terminus) antibodies were purchased from Santa Cruz Biotechnology. Mouse anti-vimentin (V9) antibody was purchased from invitrogen. Anti-P-selectin (AK4) blocking antibody was purchased from Biolegend. Mouse IgG control and anti-PSGL-1 (KPL-1) blocking antibody were purchased from BD. HUVEC were purchased from Lonza (Clonetics). Fibronectin was purchased from Advance Biomatrix. BioFlux microfluidic plates were purchased from Fluxion Biosciences. CMS sensor chips were purchased from GE Healthcare. Amine reactive $2^{nd}$ generation sensors were purchased from Pall ForteBio LLC. Endotoxin (LPS; *Escherichia coli* O111:B4) was purchased from Sigma-Aldrich.

Figure 9:
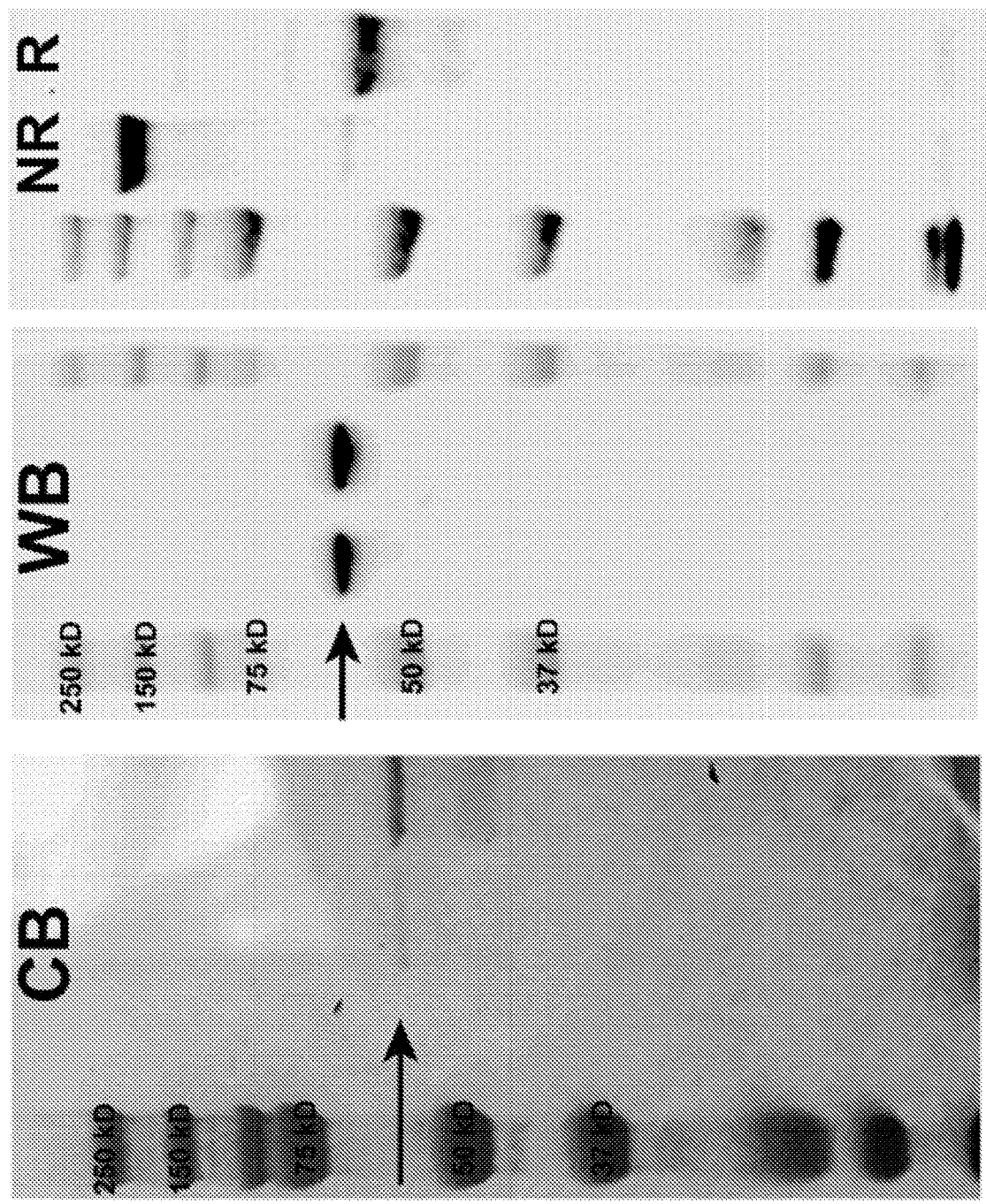
FIG. 9 shows that rhVim migrated with the expected molecular weight of 57 kDa as detected with Coomassie stain (CB) and Western blot (WB). (Right gel) Coomassie stain of rhVim under non-reduced (NR) and reduced (R) conditions.

Generation of recombinant vimentin—Human vimentin sequence was synthesized using sequence NM_003380.3 (NCBI) from nucleotides 418 to 1,814 (the mRNA sequence) and placed to pQE-30 plasmid (GenScript). The result pQE-30-hVim plasmid was transformed into *Escherichia coli* (strain M15) for protein expression following IPTG induction. The *E. coli* bacteria were pelleted down and lysed to obtain inclusion bodies. Then the inclusion body pellets were lysed with lysis buffer (6 M guanidine hydrochloride, 25 mM Tris, pH 7.4), supplemented with 1× protease inhibitor at room temperature for 2 h with constant stirring. Bacterial lysates were then centrifuged at 19,000 rpm and the supernatants filtered using a 0.45 µm filter before loading onto the $Ni^{2+}$ affinity column which had been equilibrated with binding buffer (7 M urea, 25mM Tris, pH 8). Bound proteins were then eluted with elution buffer (200 mM imidazole, 8 M urea, 25 mM Tris, pH 8). The purified sample was then serially dialyzed against decreasing concentrations of urea in Tris buffer at 4° C. Samples were ultimately dialyzed against 20 mM sodium phosphate buffer, pH 8, overnight at 4° C. and then filtered using a 0.22 µm filter under sterile conditions. Absorbance was measured at 280 nm to determine protein concentration using an extinction coefficient of 21,425 L/mol/cm and molecular weight of approximately 57 kD. Purity was confirmed using both Coomassie Blue stain and Western blot using an HRP-conjugated anti-polyhistidine antibody under reduced and non-reduced conditions (FIG. 9). Recombinant human vimentin was then stored at 4° C. until use, with new protein purified monthly. The ultimate dialysis buffer was used as the negative (vehicle) control. In some experiments, rhVim was boiled for 20 minutes to heat-denature the protein for use as a secondary, protein control.

Figure 17:
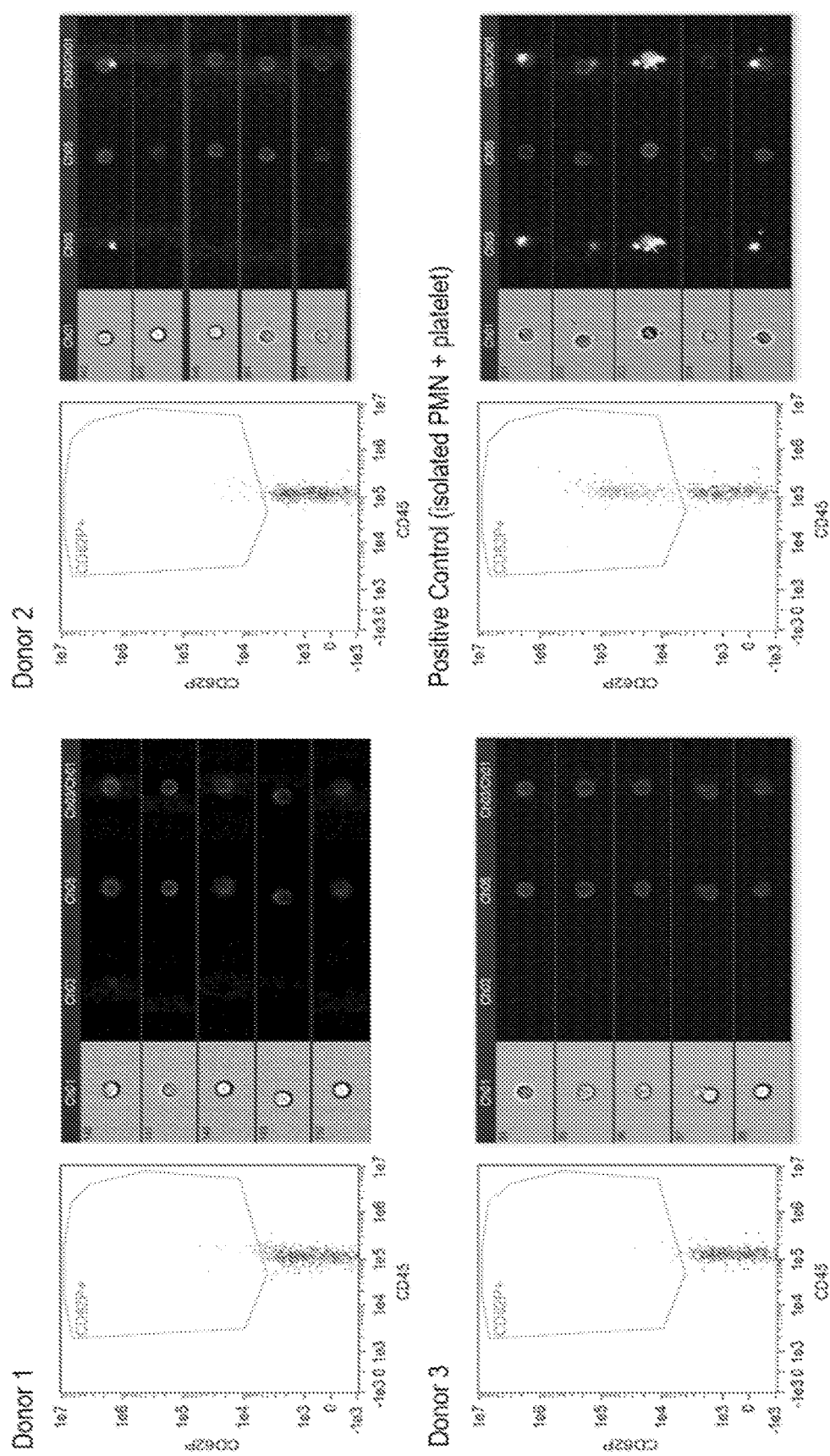
FIG. 17 provides imaging flow cytometry data of isolated PMN stained with CD62P (P-selectin) and CD45 antibodies of 3 representative donors. The Positive Control image includes isolated platelets mixed with isolated PMN. The images represent the brightfield (Ch01), CD62P (Ch03), and CD45 (Ch05) channels. Note the minimal amount of P-selectin signal on isolated PMN as compared to the signal found on PMN mixed with platelets.

Blood collection—After informed consent was obtained, blood was collected from healthy, unmedicated adult human subjects. To determine the effect of soluble vimentin in whole blood, 3.2% citrated whole blood (1:9) was labeled with 10 µM mepacrine for 20 minutes at 37° C. in order to label platelets and leukocytes (Fernandes, et al., 2003). To assess the effect of soluble vimentin on isolated platelets and neutrophils, whole blood was processed as previously described to collect washed platelets (Lam, et al., 2013) and neutrophils (Lam, et al., 2011). In some experiments, isolated neutrophils were labeled with mepacrine as above for better visualization. The purity of isolated PMN was evaluated by flow cytometry using the ImageStream Mark II imaging flow cytometer (Amnis; Millipore Sigma). Isolated PMN were labeled with anti-CD45/APC and anti-CD62P/PE antibodies (BD Pharmingen) to determine the presence of P-selectin on isolated PMN, if any. As positive control, isolated platelets were added to isolated PMN and similarly labeled for flow cytometry. In our study, <3% of isolated PMN were $CD62P^+$ as compared to 34% when isolated platelets were added to isolated PMN (FIG. 17).

In vitro parallel plate flow adhesion studies—Parallel plate flow adhesion studies were performed using BioFlux microfluidic plates as we described (Da, et al., 2015). All assays were imaged using the fluorescein isothiocyanate (FITC) channel (200 ms exposure) and a 10× objective lens (Zeiss); this allowed for image capture of 2 channels within a single field of view. Both static and time-series images (100 frames) were captured. Images were analyzed using ImageJ software (NIH). PMN imaged were counted as captured or adhered within identical areas of study. Rolling analyses were performed on 20 random PMN per channel and the results averaged based on distance traveled within 100 frames (200 ms per frame) or until the PMN was outside the field of view.

To study the effect of rhVim on leukocyte-platelet interactions in whole blood, channels were first coated with fibrinogen (100 µg/mL) for 1 hour at room temperature in order to capture platelets (Da, et al., 2015). The channels were washed with DPBS without calcium or magnesium (pH 7.2-7.4) to remove excess fibrinogen. Mepacrine-labeled whole blood, in the presence of rhVim or vehicle, was then perfused over fibrinogen-coated chambers at 4 dyn/cm$^2$ for 10 minutes to allow for initial platelet activation and adhesion to fibrinogen. The shear stress was then reduced to 2 dyn/cm$^2$ and images were recorded for 10 minutes to study leukocyte-platelet adhesion in the presence of rhVim.

To study the effect of rhVim on adhesion of isolated neutrophils, channels were first coated with isolated platelets (400×10$^6$/mL) for 1 hour at room temperature, fibrin(ogen) (100 µg/mL), or no coating. Channels were washed with DPBS without calcium or magnesium. Mepacrine-labeled neutrophils (4×10$^6$/mL) were then perfused through the channels in the presence of various concentrations of rhVim, blocking antibodies to P-selectin and PSGL-1 were used as positive controls. Additional experiments were performed in using of channels coated with P-selectin/Fc chimeric protein (10 µg/ml) to determine the effect of rhVim on neutrophil adhesion to P-selectin.

To study the effect of rhVim on leukocyte adhesion to endothelium, microfluidic channels were coated with fibronectin (100 µg/mL) for 1 hour at room temperature. HUVEC (passage 2 or 3) were seeded in the channels and incubated at 37° C/5% $CO_2$. Once the HUVEC reached confluence, they were stimulated with rhIL-1β (10 U/mL) for 4 hours at 37° C. to activate them (Lam, et al., 2011). Then mepacrine-labeled whole blood or isolated PMN was perfused (2 dyn/cm$^2$) over IL-1β-stimulated HUVEC in the presence of rhVim or boiled rhVim. Images were recorded as above.

rhVim binding assay—To determine which proteins to which rhVim binds, we performed enzyme linked immunosorbent assays (ELISA) as we described (Da, et al., 2014). Immunoplate wells were coated overnight at 4° C. with P-selectin/Fc or PSGL-1/Fc (10 µg/ml in DPBS). Wells were washed with DPBS and then blocked with 1% BSA for one hour. After blocking, rhVim was added in increasing concentrations and detected using a HRP-conjugated anti-polyhistidine antibody. Tetramethylbenzidine solution was used as the substrate and the reactions were stopped using 1 N sulfuric acid. All ELISA measurements were performed in duplicate and the data reported were averaged from two separate experiments performed.

Surface plasmon resonance—To determine the binding affinity of P-selectin and E-selectin to rhVim, we measured the equilibrium dissociation constant, $K_D$, of P-selectin binding to rhVim using surface plasmon resonance (SPR; BIACore; GE Healthcare) (Dong, et al., 2003). Fifteen µg/mL of rhVim (diluted in 10 mM sodium acetate pH 4.5) was immobilized on CM5 sensor chips using 0.1 M N-hydroxysuccinimide (NHS) and 0.4 M 1-ethyl-3-(3-dimethylaminopropyl)-carbodiimide (EDC). The amine coupling reaction was quenched with 1 M ethanolamine-HCl, pH 8.5. P-selectin/Fc, E-selectin/Fc, or human IgG (control) was then perfused over the chip using a concentration range of 10-1,000 nM. Regeneration was performed using 20 mM sodium hydroxide and 10 mM glycine, pH 2. DPBS was used as the running buffer. Data were analyzed using BIACore analysis software to determine the $K_D$.

Bio-layer interferometry—In addition to SPR, we used bio-layer interferometry (BLI; Octet Red 384; Pall ForteBio LLC) to determine the KD of P-selectin, E-selectin, and PSGL-1 to rhVim. We immobilized rhVim 50 µg/mL onto amine reactive 2$^{nd}$ generation sensors (Pall ForteBio LLC) using NHS and EDC. The amine coupling reaction was quenched with 1 M ethanolamine-HCl, H 8.5, and then washed with DPBS. rhVim-immobilized sensors were then used to assess binding kinetics to the following analytes at concentrations ranging 0-1,000 nM (diluted in DPBS): P-selectin/Fc, E-selectin/Fc, PSGL-1/Fc, human IgG and sheep anti-vimentin antibody. We also performed BLI to determine whether rhVim (30 µg/mL) bound to the following immobilized (onto amine reactive 2$^{nd}$ generation sensors as above) commercial anti-vimentin antibodies (10 µg/mL): H-84, C-20, E-5, V9, and sheep anti-vimentin antibodies (FIG. 10). All buffers used for association and dissociation kinetics were DPBS. Regeneration was performed using 10 mM glycine, pH 1.75. Data were analyzed using Octet System Data Analysis software (Pall ForteBio LLC).

Endotoxin-induced murine acute lung injury—Male and female C57B1/6J wild-type mice, ages 10-11 weeks, were used for this study. To assess whether rhVim would decreased leukocyte accumulation into inflamed lungs, mice were first injected intraperitoneally (i.p.) with 3 mg/kg of rhVim followed one hour later by a sub-lethal dose of LPS (15 mg/kg i.p.). Blinded investigators evaluated the mice based on the mouse clinical activity score for sepsis (Huet, et al., 2013). Ninety-six hours after LPS injection, mice were euthanized under a surgical plane of anesthesia. Lung fixation was accomplished by intratracheal instillation of 10% formalin in situ fixation. The trachea was tied with surgical suture to maintain inflated lung tissue for proper fixation. Tissues were then submerged in 10% for 72 hours prior to tissue processing and paraffin embedding. Tissues were sectioned at 5 µm thick and stained with hematoxylin and eosin (H&E). Slides were prepared with hematoxylin and eosin (H&E) and images were captured on an Olympus BX61 microscope with a JVC KY-F75U camera with ImageJ Micro Manager software. Two blinded investigators scored the H&E sections for histologic acute lung injury using the method defined by the American Thoracic Society (Matute-Bello, et al., 2008). Briefly, 20 random 400× fields were imaged and then independently scored using a weighted average evaluating (a) number of alveolar neutrophils, (b) number of interstitial neutrophils, (c) presence of hyaline membranes, (d) proteinaceous material filling alveoli, and (e) alveolar wall thickness. The weighted average provides a score between 0 and 1, with 1 being the most severe. The scores are then averaged to determine the score for that animal.

Statistical analysis—Data analysis was performed using Prism 6 (Graphpad Software Inc). In vitro data were analyzed using either Student's paired t-tests, repeated measures analysis of variance (ANOVA) with Dunnett's multiple comparison test, or 2-way repeated measures ANOVA with Bonferroni's multiple comparison test, where appropriate. In vivo data were analyzed using Student's t-test. A p-value<0.05 was considered significant. KD values in which $R^2$<0.8 were considered indeterminate.

Figure 11A:
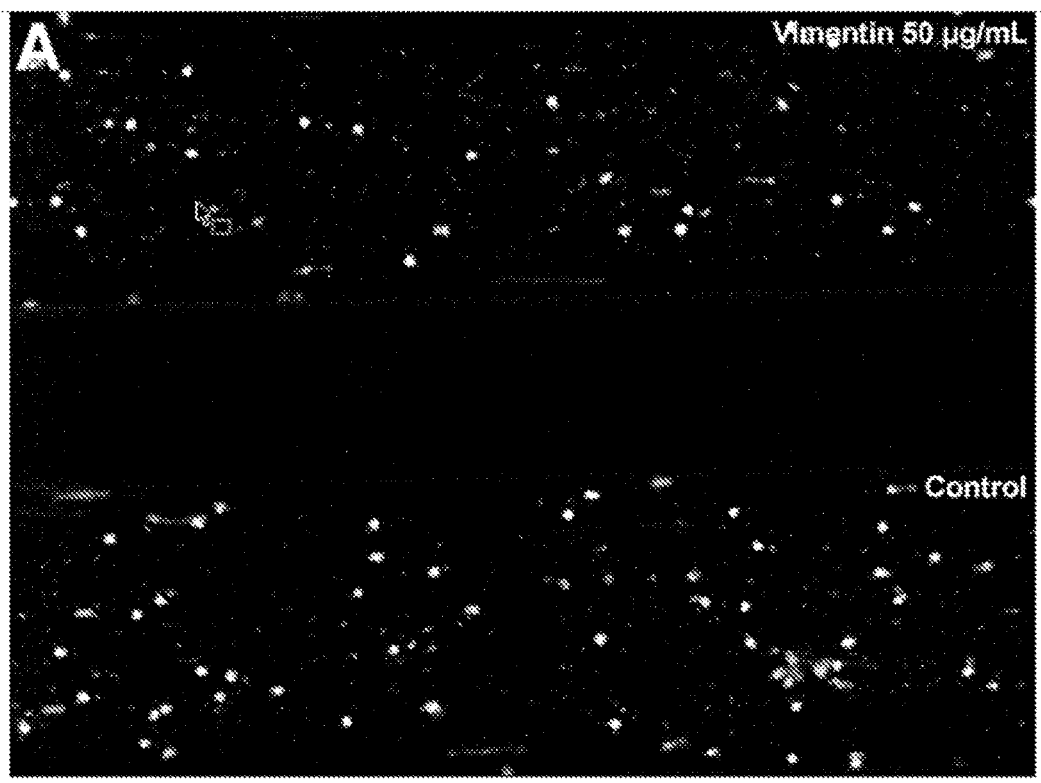
FIGS. 11A and 11B provide that whole blood labeled with mepacrine was perfused over fibrin(ogen)-coated channels with or without rhVim.
Figure 11B:
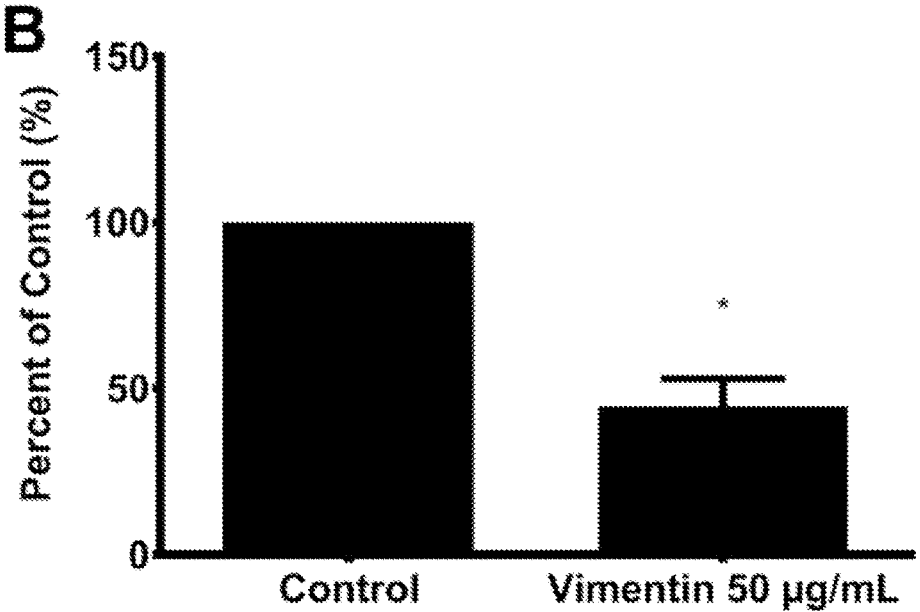
Figure 12A:
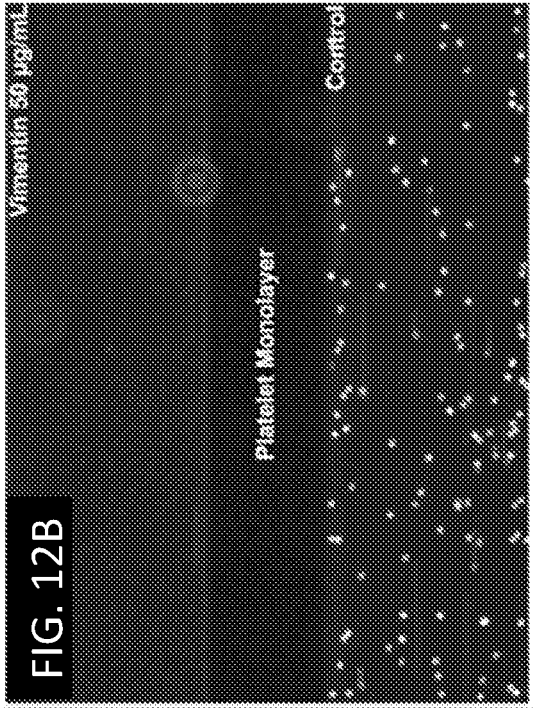
(FIG. 12D) rhVim significantly decreased PMN adhesion to platelet monolayers and had no effect on PMN adhesion to immobilized fibrin(ogen) or glass (none). *$p<0.05$, n=3 repeated subjects.
Figure 12B:
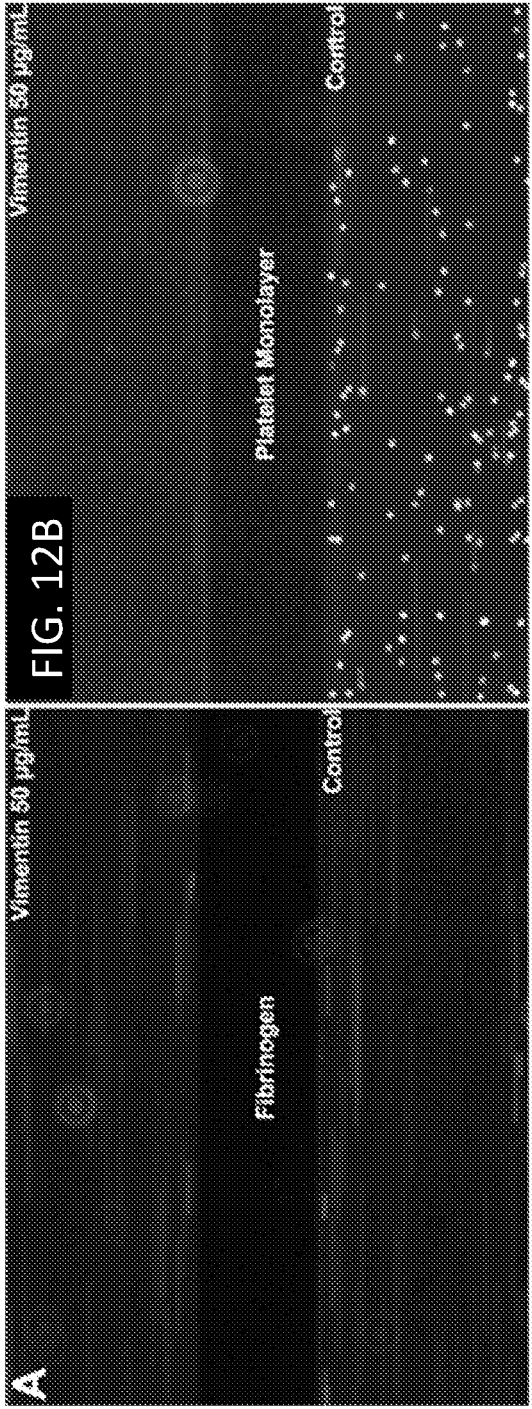
Figure 12C:
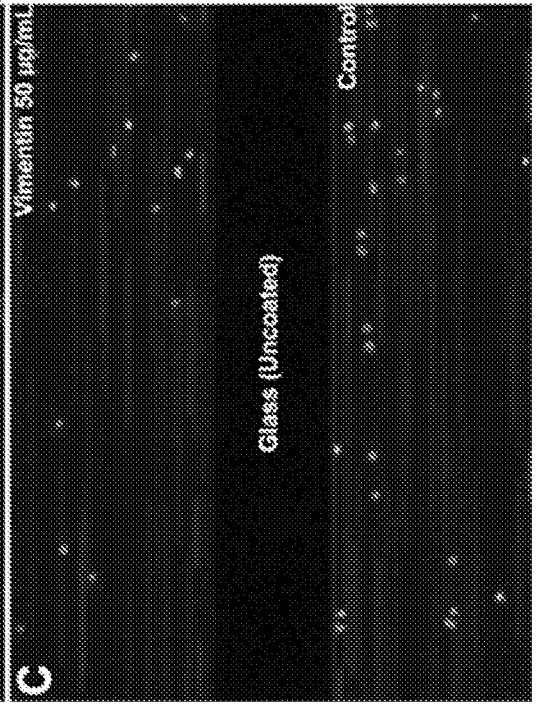
Figure 12D:
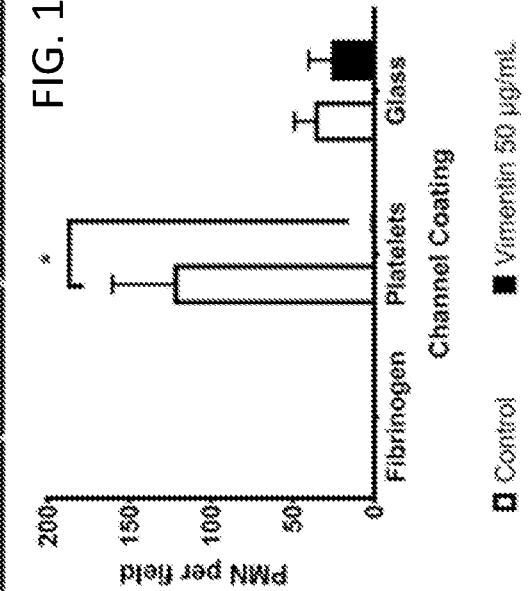
Figure 13A:
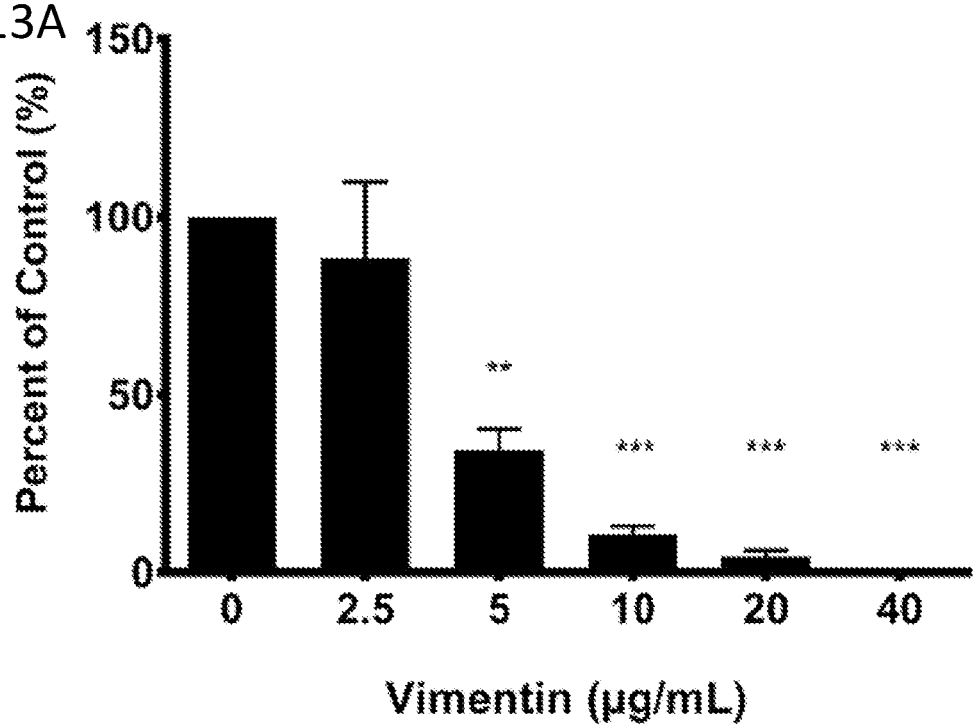
FIGS. 13A and 13B.
Figure 13B:
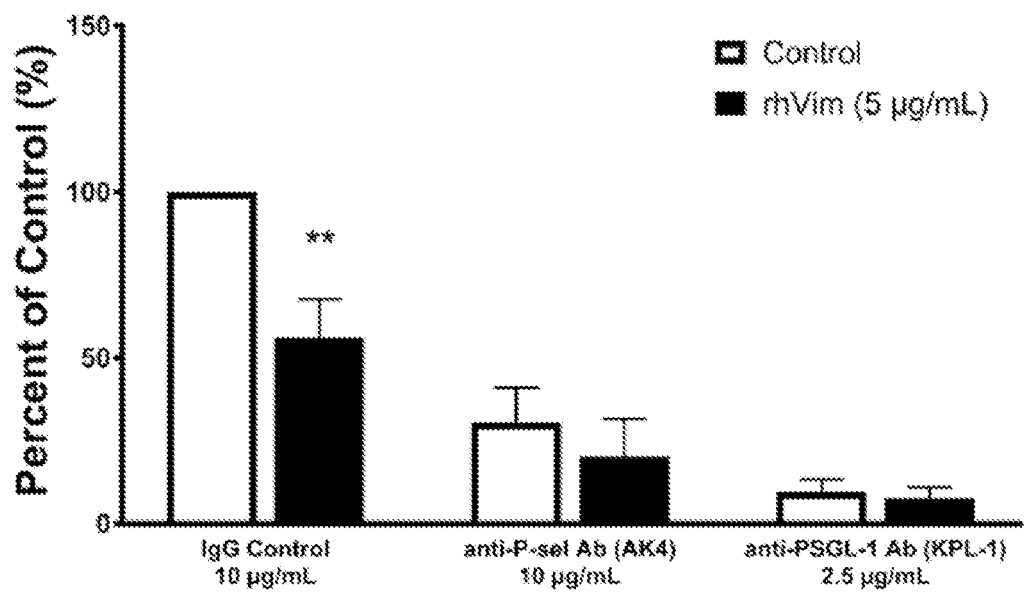
Figure 14A:
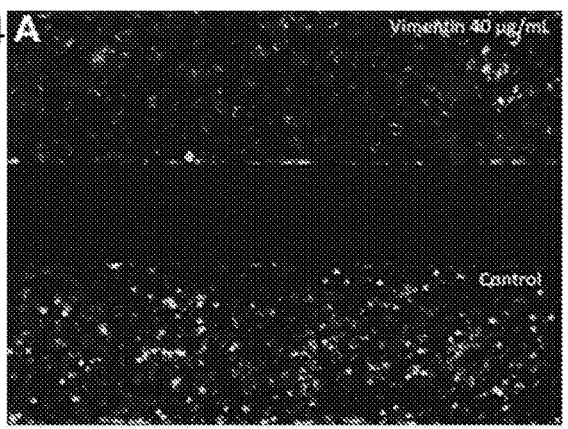
FIGS. 14A-14E.
Figure 14B:
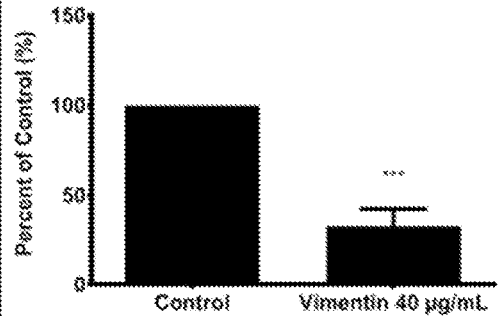

Examples of Results rhVim decreases WBC adhesion to fibrinogen coated channels—Based on previous reports of vimentin being secreted and its ability to bind to N-acetylglucosamine, the effect of rhVim on WBC capture and adhesion was studied. The inventors perfused (2 dyn/cm$^2$) mepacrine-labeled whole blood over surfaces coated with fibrin(ogen), which exposes fibrin-specific sequences upon surface adsorption (FIG. 11A). In this assay, platelets adhere to fibrin(ogen) and become activated, consequently capturing the flowing WBC. The addition of rhVim had no differences in platelet adhesion to the fibrin(ogen) surface based on fluorescence imaging. However, rhVim 50 μg/mL significantly decreased the number of adhered WBC flowing over fibrin(ogen) monolayers by approximately 55% (FIG. 11B).

rhVim decreases human neutrophil (PMN) adhesion to platelet monolayers in a dose dependent fashion—To determine whether our observations that rhVim decreases WBC adhesion to fibrin(ogen) is due to disruption of WBC-fibrinogen interactions (Altieri, et al., 1990) or WBC-platelet interaction (Diacovo, et al., 1996; Lam, et al., 2011) we perfused isolated human PMN over microfluidic channels coated with fibrin(ogen), platelets, or no coating (glass; FIG. 12A-12C). Isolated PMN did not adhere to fibrin(ogen), with or without rhVim. Additionally, PMN adhesion to glass was not affected by the presence of rhVim. However, the presence of rhVim significantly decreased PMN adhesion to platelet monolayers (FIG. 12D). Furthermore, rhVim decreased PMN adhesion to platelet monolayers in a dose-dependent manner, with maximal inhibition at a rhVim concentration of 40 μg/mL (FIG. 13A). Blocking antibodies to P-selectin (AK4; 10 μg/mL) and PSGL-1 (KPL-1; 2.5 μg/mL) similarly blocked PMN adhesion to platelet monolayers. However, the addition of rhVim 5 μg/mL to either AK4 or KPL-1 did not further decrease PMN adhesion to platelet monolayers (FIG. 13B).

rhVim decreases human leukocyte adhesion to IL-1,8 stimulated human umbilical vein endothelial cells (HUVEC)—In addition to its effect on platelet-neutrophil interactions, we tested whether rhVim also impairs the capture and adhesion of neutrophils to endothelial cells. HUVEC were cultured on fibronectin-coated channels (FIG. 14A), and once the HUVEC reached 100% confluence, they were stimulated with rhIL-1β for 4 hours (Lam, et al., 2011). The inventors then perfused isolated PMN in the presence of rhVim (40 μg/mL) or vehicle control over the HUVEC monolayer. The presence of rhVim significantly decreased the number of adherent PMN to HUVEC monolayers by ~67% (FIG. 14B).

Figure 14C:
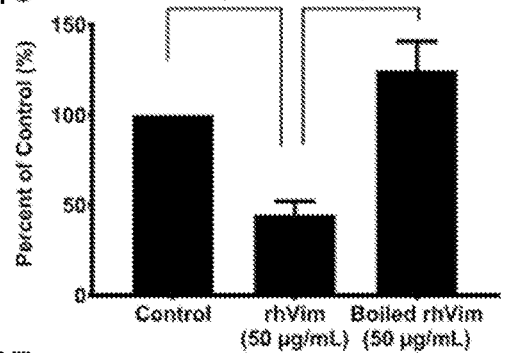
Figure 14D:
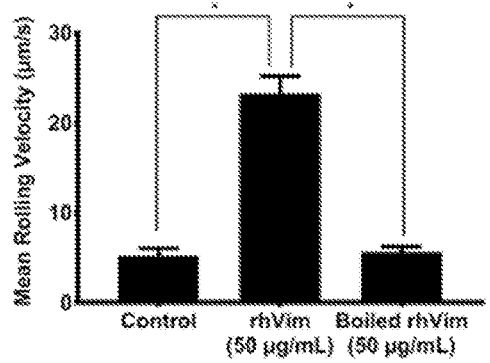

The effect of rhVim (50 μg/mL) was compared to both vehicle control as well as to boiled rhVim (50 μg/mL) to determine whether the effects on PMN adhesion to HUVEC was specifically due to rhVim. Like previous observations, rhVim significantly decreased PMN adhesion to HUVEC monolayers as compared to both vehicle control and boiled rhVim. Furthermore, there was no difference in PMN adhesion between vehicle control and boiled rhVim (FIG. 14C). Similarly, average PMN rolling velocity was significantly increased in the presence of rhVim as compared to vehicle and boiled rhVim controls (FIG. 14D).

Figure 14E:
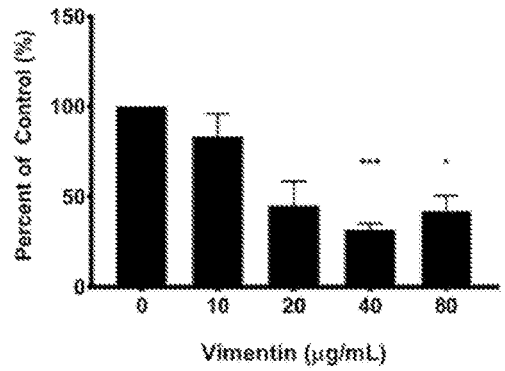
Figure 15A:
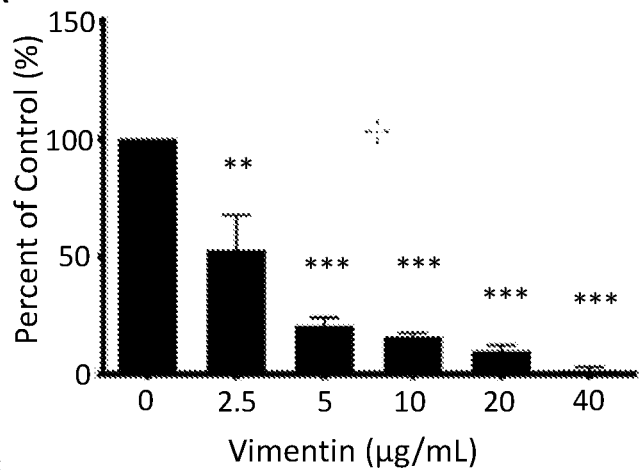
FIGS. 15A-15C.
Figure 15B:
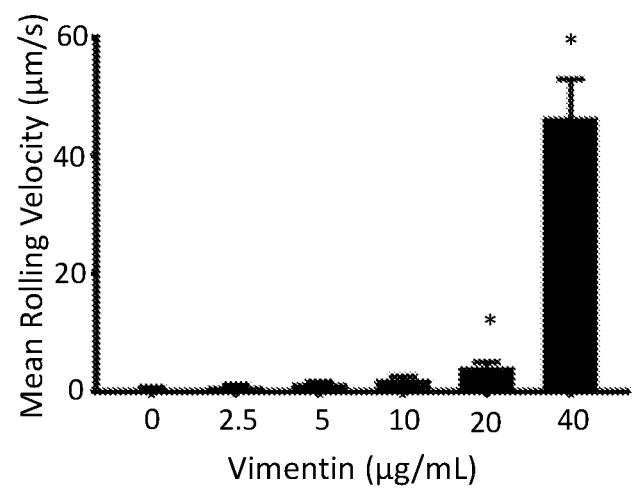

Based on these observations, the effect of rhVim on leukocyte capture onto HUVEC when mixed in whole blood was tested. Mepacrine-labeled whole blood was perfused over IL-1β-stimulated HUVEC in the presence of increasing concentrations of rhVim. Similar to its effect on isolated PMN, rhVim blocked leukocyte capture and adhesion to HUVEC monolayers by ~60% (FIG. 14E).

rhVim binds to P-selectin, but not PSGL-1, to decrease human neutrophil adhesion to P-selectin/Fc chimeric protein in a dose dependent fashion—Because of the multiple adhesive interactions between PMN and platelets, the cell adhesion molecules were considered. Isolated PMN were perfused over channels coated with P-selectin/Fc chimeric protein (10 μg/mL) in the presence of increasing concentrations of rhVim. Similar to observations with platelet monolayers, the presence of rhVim decreased PMN adhesion to P-selectin/Fc monolayers in a dose-dependent fashion (FIG. 15A). Furthermore, the addition of rhVim increased the mean rolling velocity of PMN over the P-selectin/Fc monolayers (FIG. 15B).

Figure 15C:
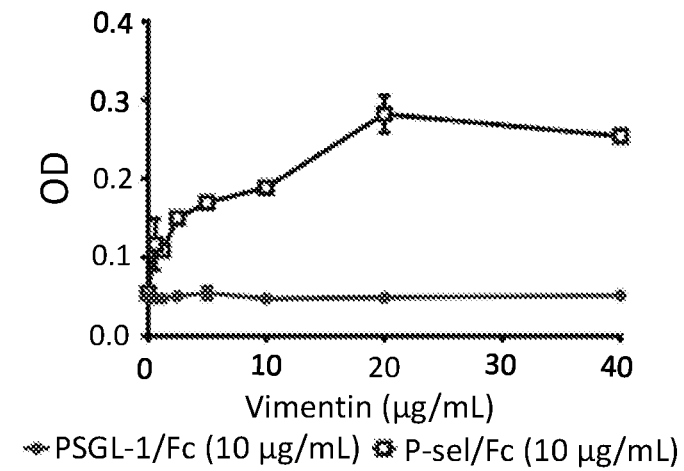

The effect of rhVim blocking PMN adhesion to P-selectin could be attributed to rhVim either affecting P-selectin, PSGL-1, or both. Therefore, ELISAs were performed with wells coated either PSGL-1/Fc protein (10 μg/mL) or P-selectin/Fc protein (10 μg/mL) and incubated with increasing concentrations of rhVim to each well. Increasing amounts of rhVim bound to P-selectin/Fc protein and reached saturation at 20 μg/mL. There was no binding of rhVim to PSGL-1/Fc at any concentration (FIG. 15C).

rhVim binds preferentially to P-selectin, and not to E-selectin or PSGL-1—Based on ELISA data that rhVim binds to P-selectin and not to PSGL-1, binding kinetics analysis was performed of P-selectin/Fc to rhVim using surface plasmon resonance, with human IgG as a control for the Fc fragment. In addition, the binding kinetics of E-selectin to rhVim was performed, because E-selectin is expressed on endothelium and participates in leukocyte capture and rolling adhesion. P-selectin/Fc exhibited strong binding to immobilized rhVim with a KD of 67±1.2 nM whereas there was no binding to either E-selectin/Fc or human IgG (Table 1).

TABLE 1

$K_D$ values to immobilized rhVim.

| Analyte | Method | $K_D$ (nM) | $R^2$ |
|---|---|---|---|
| P-selectin/Fc | SPR | 67 ± 1.2 | 1 |
|  | BLI | 53 ± 16 | 0.898 |
| E-selectin/Fc | SPR | Indeterminate | N/A |
|  | BLI | 6.5 ± 12 | 0.066 |
| PSGL-1/Fc | BLI | Indeterminate | N/A |
| Human IgG | SPR | Indeterminate | N/A |
|  | BLI | 7.1 ± 13 | 0.092 |
| Sh anti-vimentin Ab | BLI | 2,300 ± 1400 | 0.969 |

SPR: surface plasmon resonance; BLI: bio-layer interferometry.

Binding kinetic analyses were performed of P-selectin/Fc, E-selectin/Fc, and PSGL-1/Fc to rhVim using bio-layer interferometry. Human IgG and sheep anti-vimentin antibody served as negative and positive controls, respectively. Similar to the ELISA and SPR data, P-selectin/Fc bound to rhVim with great affinity, with a $K_D$ of 53±16 nM. However, neither E-selectin/Fc nor PSGL-1/Fc bound to rhVim (Table 1). There was no binding to human IgG and expected binding to sheep anti-vimentin antibody.

Treatment with rhVim decreased histologic evidence of acute lung injury—It has been established that P-selectin-PSGL-1 interactions have been implicated in animal models of acute lung injury (Zarbock, et al., 2006). Therefore, based on at least in vitro data, it was considered that rhVim has a beneficial role in attenuating inflammation in vivo. There were no differences in mortality when using the sub-lethal dose of LPS. However, mice receiving rhVim had a significantly lower histologic acute lung injury score than mice receiving vehicle control, with decreased neutrophilic infiltration into the lungs (FIG. 16).

Experiments using whole blood perfused over fibrinogen coated plates include the following:

(a) Whole blood collected from healthy donors;

(b) Whole blood samples were aliquoted to similar volumes (200 uL)

(c) To each aliquot, either FULL vimentin, ROD vimentin (the rod domain), or buffer control was added (d) The whole blood sample with additive was perfused over fibrinogen coated microchannels at 4 dyn/cm2 to allow platelets to adhere to the fibrinogen without leukocyte adhesion. The shear was dropped to 2 dyn/cm$^2$ to evaluate leukocyte adhesion to platelets. The presence of ROD appears to also inhibit leukocyte adhesion.

One can also coat microchannels with P-selectin/Fc protein and perfuse isolated neutrophils in the presence of ROD vs. control buffer to determine if ROD behaves similarly to FULL vimentin in blocking PMN from binding to P-sel/Fc coated surfaces. One can inject endotoxemic mice with ROD, similar to studies described elsewhere herein with regard to FULL vimentin. One can label ROD with a fluorescent dye and inject it into mice to evaluate pharmacokinetics and localization.

One can utilize another model of inflammation, which is corneal abrasion. This is a sterile model of inflammation in which platelets play a key role in neutrophil migration (Lam et al., 2010). In one study, mice were injected IP with either FULL vimentin or buffer control, and then one hour later mice were anesthetized and their corneas abraded. Twelve hours after abrasion, mice were euthanized and their corneas collected and processed for imaging of blood vessels, platelets, and neutrophils. In specific embodiments, mice receiving FULL vimentin have decreased neutrophil accumulation in the eye compared to mice receiving control.

REFERENCES

All publications mentioned in this specification are indicative of the level of those skilled in the art to which the invention pertains. All publications herein are incorporated by reference to the same extent as if each individual publication was specifically and individually indicated to be incorporated by reference in their entirety.

Abrams S T, Zhang N, Manson J, Liu T, Dart C, Baluwa F, et al. Circulating histones are mediators of trauma-associated lung injury. American Journal of Respiratory and Critical Care Medicine. 2013 Jan. 15; 187(2):160-169.

Altieri, D. C., F. R. Agbanyo, J. Plescia, M. H. Ginsberg, T. S. Edgington, and E. F. Plow. 1990. A unique recognition site mediates the interaction of fibrinogen with the leukocyte integrin Mac-1 (CD11b/CD18). *J Biol Chem* 265: 12119-12122.

Asaduzzaman, M., S. Lavasani, M. Rahman, S. Zhang, O. O. Braun, B. Jeppsson, and H. Thorlacius. 2009. Platelets support pulmonary recruitment of neutrophils in abdominal sepsis. *Crit Care Med* 37: 1389-1396.

Asaduzzaman, M., M. Rahman, B. Jeppsson, and H. Thorlacius. 2009. P-selectin glycoprotein-ligand-1 regulates pulmonary recruitment of neutrophils in a platelet-independent manner in abdominal sepsis. *British Journal of Pharmacology* 156: 307-315.

Bay-Jensen, A. C., M. A. Karsdal, E. Vassiliadis, S. Wichuk, K. Marcher-Mikkelsen, R. Lories, C. Christiansen, and W. P. Maksymowych. 2013. Circulating citrullinated vimentin fragments reflect disease burden in ankylosing spondylitis and have prognostic capacity for radiographic progression. *Arthritis Rheum* 65: 972-980.

Bellani G, Laffey J G, Pham T, Fan E, Brochard L, Esteban A, et al. Epidemiology, Patterns of Care, and Mortality for Patients With Acute Respiratory Distress Syndrome in Intensive Care Units in 50 Countries. JAMA. American Medical Association; 2016 Feb. 23; 315(8):788-800.

Blank R, Napolitano L M. Epidemiology of ARDS and ALI. Crit Care Clin. 2011 July; 27(3):439-458.

Bode G, Clausing P, Gervais F, Loegsted J, Luft J, Nogues V, et al. The utility of the minipig as an animal model in regulatory toxicology. J Pharmacol Toxicol Methods. 2010 May 31; 62(3):196-220.

Brentville, V. A., R. L. Metheringham, B. Gunn, P. Symonds, I. Daniels, M. Gijon, K. Cook, W. Xue, and L. G. Durrant. 2016. Citrullinated Vimentin Presented on MHC-II in Tumor Cells Is a Target for CD4+ T-Cell-Mediated Antitumor Immunity. *Cancer research* 76: 548-560.

Burns A R, Walker D C, Brown E S, Thurmon L T, Bowden R A, Keese C R, et al. Neutrophil transendothelial migration is independent of tight junctions and occurs preferentially at tricellular corners. J Immunol. 1997 Sep. 15; 159(6):2893-2903.

Caudrillier A, Kessenbrock K, Gilliss B M, Nguyen J X, Marques M B, Monestier M, et al. Platelets induce neutrophil extracellular traps in transfusion-related acute lung injury. J Clin Invest. 2012 Jun. 11; 122(7):2661-2671.

Chernyatina, A. A., S. Nicolet, U. Aebi, H. Herrmann, and S. V. Strelkov. 2012. Atomic structure of the vimentin central alpha-helical domain and its implications for intermediate filament assembly. *Proceedings of the National Academy of Sciences of the United States of America* 109: 13620-13625.

Craig A, Mai J, Cai S, Jeyaseelan S. Neutrophil recruitment to the lungs during bacterial pneumonia. Infect Immun. American Society for Microbiology; 2009 February; 77(2): 568-575.

Da, Q., M. Behymer, J. I. Correa, K. V. Vijayan, and M. A. Cruz. 2014. Platelet adhesion involves a novel interaction between vimentin and von Willebrand factor under high shear stress. *Blood* 123: 2715-2721.

Da, Q., M. Teruya, P. Guchhait, J. Teruya, J. S. Olson, and M. A. Cruz. 2015. Free hemoglobin increases von Willebrand factor-mediated platelet adhesion in vitro: implications for circulatory devices. *Blood* 126: 2338.

Diacovo, T. G., S. J. Roth, J. M. Buccola, D. F. Bainton, and T. A. Springer. 1996. Neutrophil rolling, arrest, and transmigration across activated, surface-adherent platelets via sequential action of P-selectin and the beta 2-integrin CD11b/CD18. *Blood* 88: 146-157.

Dong, J. F., J. L. Moake, L. Bernardo, K. Fujikawa, C. Ball, L. Nolasco, J. A. Lopez, and M. A. Cruz. 2003. ADAMTS-13 metalloprotease interacts with the endothelial cell-derived ultra-large von Willebrand factor. *J Biol Chem* 278: 29633-29639.

Feng S, Liang X, Vu H, Zhou Z, Pemmaraju N, Dong J-F, et al. The Interaction between Factor H and Von Willebrand Factor. PLoS ONE. 2013; 8(8):e73715.

Fernandes L S, Conde I D, Wayne Smith C, Kansas G S, Snapp K R, Bennet N, et al. Platelet-monocyte complex formation: effect of blocking PSGL-1 alone, and in combination with alphaIIbbeta3 and alphaMbeta2, in coronary stenting. Thromb Res. 2003; 111(3):171-177.

Fortenberry, J. D., V. Bhardwaj, P. Niemer, J. D. Cornish, J. A. Wright, and L. Bland. 1996. Neutrophil and cytokine activation with neonatal extracorporeal membrane oxygenation. *J Pediatr* 128: 670-678.

Forster R, Bode G, Ellegaard L, van der Laan J-W. The RETHINK project on minipigs in the toxicity testing of new medicines and chemicals: conclusions and recommendations. J Pharmacol Toxicol Methods. 2010 May 31; 62(3): 236-242.

Ganter, M. T., J. Roux, B. Miyazawa, M. Howard, J. A. Frank, G. Su, D. Sheppard, S. M. Violette, P. H. Weinreb, G. S. Horan, M. A. Matthay, and J. F. Pittet. 2008. Interleukin- 1beta causes acute lung injury via alphavbeta5 and alphavbeta6 integrin-dependent mechanisms. *Circ Res* 102: 804-812.

Hanley, W. D., S. L. Napier, M. M. Burdick, R. L. Schnaar, R. Sackstein, and K. Konstantopoulos. 2006. Variant isoforms of CD44 are P- and L-selectin ligands on colon carcinoma cells. *FASEB J* 20: 337-339.

Huet O, Ramsey D, Miljavec S, Jenney A, Aubron C, Aprico A, et al. Ensuring Animal Welfare While Meeting Scientific Aims Using a Murine Pneumonia Model of Septic Shock. Shock. 2013 June; 39(6):488-494.

Iskander K N, Osuchowski M F, Stearns-Kurosawa D J, Kurosawa S, Stepien D, Valentine C, et al. Sepsis: multiple abnormalities, heterogeneous responses, and evolving understanding. Physiological Reviews. 2013 July; 93(3): 1247-1288.

Ise H, Kobayashi S, Goto M, Sato T, Kawakubo M, Takahashi M, et al. Vimentin and desmin possess GlcNAc-binding lectin-like properties on cell surfaces. Glycobiology. 2010 Mar. 22; 20(7): 843-864.

Ivaska J, Pallari H-M, Nevo J, Eriksson J E. Novel functions of vimentin in cell adhesion, migration, and signaling. Exp Cell Res. 2007 Jun. 10; 313(10):2050-2062.

Jones D A, Abbassi O, McIntire L V, McEver R P, Smith C W. P-selectin mediates neutrophil rolling on histamine-stimulated endothelial cells. Biophys J. 1993 Oct. 1; 65(4): 1560-1569.

Katayama, Y., A. Hidalgo, J. Chang, A. Peired, and P. S. Frenette. 2005. CD44 is a physiological E-selectin ligand on neutrophils. *J Exp Med* 201: 1183-1189.

Kolb, M., P. J. Margetts, D. C. Anthony, F. Pitossi, and J. Gauldie. 2001. Transient expression of IL-lbeta induces acute lung injury and chronic repair leading to pulmonary fibrosis. *J Clin Invest* 107: 1529-1536.

Konstantopoulos K, Neelamegham S, Burns A R, Hentzen E, Kansas G S, Snapp K R, et al. Venous levels of shear support neutrophil-platelet adhesion and neutrophil aggregation in blood via P-selectin and beta2-integrin. Circulation. 1998 Sep. 1; 98(9):873-882.

Kuijper P H, Gallardo Torres H I, Lammers J W, Sixma J J, Koenderman L, Zwaginga J J. Platelet and fibrin deposition at the damaged vessel wall: cooperative substrates for neutrophil adhesion under flow conditions. Blood. 1997 Jan. 1; 89(1):166-175.

Kumar, A., V. Thota, L. Dee, J. Olson, E. Uretz, and J. E. Parrillo. 1996. Tumor necrosis factor alpha and interleukin lbeta are responsible for in vitro myocardial cell depression induced by human septic shock serum. *J Exp Med* 183: 949-958.

Lam F W, Burns A R, Smith C W, Rumbaut R E. Platelets enhance neutrophil transendothelial migration via P-selectin glycoprotein ligand-1. AJP: Heart and Circulatory Physiology. 2011 February; 300(2):H468-75.

Lam F W, Cruz M A, Leung H-C E, Parikh K S, Smith C W, Rumbaut R E. Histone induced platelet aggregation is inhibited by normal albumin. Thromb Res. 2013 July; 132(1):69-76.

Lam F W, Rumbaut R E, Burns A R. Mechanisms of neutrophil migration. In: Gabrilovich DI, editor. 3rd ed. London: Imperial College Press; 2013. pp. 129-188.

Lam F W, Vijayan K V, Rumbaut R E. Platelets and Their Interactions with Other Immune Cells. Compr Physiol. Hoboken, N.J., USA: John Wiley & Sons, Inc; 2015 Jul. 1; 5(3):1265-1280.

Lerman Y V, Lim K, Hyun Y-M, Falkner K L, Yang H, Pietropaoli A P, et al. Sepsis lethality via exacerbated tissue infiltration and TLR-induced cytokine production by neutrophils is integrin α3β1-dependent. Blood. 2014 Dec. 4; 124(24):3515-3523.

Li, Z., R. E. Rumbaut, A. R. Burns, and C. W. Smith. 2006. Platelet response to corneal abrasion is necessary for acute inflammation and efficient re-epithelialization. *Invest Ophthalmol Vis Sci* 47: 4794-4802.

Li, F. J., R. Surolia, H. Li, Z. Wang, T. Kulkarni, G. Liu, J. A. de Andrade, D. J. Kass, V. J. Thannickal, S. R. Duncan, and V. B. Antony. 2017. Autoimmunity to Vimentin Is Associated with Outcomes of Patients with Idiopathic Pulmonary Fibrosis. *J Immunol* 199: 1596-1605.

Li Z, Burns A R, Smith C W. Two waves of neutrophil emigration in response to corneal epithelial abrasion: distinct adhesion molecule requirements. Investigative Ophthalmology & Visual Science. 2006 May; 47(5):1947-1955.

Lichenstein, H. S., D. F. Bainton, K. D. Patel, F. Li, R. P. McEver, D. A. Johnson, R. D. Cummings, K. L. Moore, and R. E. Bruehl. 1995. P-selectin glycoprotein ligand-1 mediates rolling of human neutrophils on P-selectin. *J Cell Biol* 128: 661-671.

Looney M R, Gropper M A, Matthay M A. Transfusion-related acute lung injury: a review. Chest. American College of Chest Physicians; 2004 July; 126(1):249-258.

Matute-Bello G, Frevert C W, Martin T R. Animal models of acute lung injury. Am J Physiol Lung Cell Mol Physiol. American Physiological Society; 2008 September; 295(3): L379-99.

McEver, R. P., and R. D. Cummings. 1997. Perspectives series: cell adhesion in vascular biology. Role of PSGL-1 binding to selectins in leukocyte recruitment. *J Clin Invest* 100: 485-491.

McEver, R. P., J. H. Beckstead, K. L. Moore, L. Marshall-Carlson, and D. F. Bainton. 1989. GMP-140, a platelet alpha-granule membrane protein, is also synthesized by vascular endothelial cells and is localized in Weibel-Palade bodies. *J. Clin. Invest.* 84: 92-99.

McILwain R B, Timpa J G, Kurundkar A R, Holt D W, Kelly D R, Hartman Y E, et al. Plasma concentrations of inflammatory cytokines rise rapidly during ECMO-related SIRS due to the release of preformed stores in the intestine. Lab Invest. 2010 January; 90(1):128-139.

Moore K L, Stults N L, Diaz S, Smith D F, Cummings R D, Varki A, et al. Identification of a specific glycoprotein ligand for P-selectin (CD62) on myeloid cells. J Cell Biol. 1992 July; 118(2):445-456.

Mor-Vaknin N, Punturieri A, Sitwala K, Markovitz D M. Vimentin is secreted by activated macrophages. Nat Cell Biol. 2003 January; 5(1):59-63.

Mor-Vaknin N, Legendre M, Yu Y, Serezani C H C, Garg S K, Jatzek A, et al. Murine colitis is mediated by vimentin. Sci Rep. 2013; 3:1045.

Murohara T, Delyani J A, Albelda S M, Lefer A M. Blockade of platelet endothelial cell adhesion molecule-1 protects against myocardial ischemia and reperfusion injury in cats. J Immunol. 1996 May 1; 156(9):3550-3557.

Nieminen M, Henttinen T, Merinen M, Marttila-Ichihara F, Eriksson J E, Jalkanen S. Vimentin function in lymphocyte adhesion and transcellular migration. Nat Cell Biol. 2006 February; 8(2): 156-162.

Pall, T., A. Pink, L. Kasak, M. Turkina, W. Anderson, A. Valkna, and P. Kogerman. 2011. Soluble CD44 interacts with intermediate filament protein vimentin on endothelial cell surface. *PLoS ONE* 6: e29305.

Podor T J, Singh D, Chindemi P, Foulon D M, McKelvie R, Weitz J I, et al. Vimentin exposed on activated platelets and platelet microparticles localizes vitronectin and plasminogen activator inhibitor complexes on their surface. J Biol Chem. 2001 Dec. 14; 277(9):7529-7539.

Rhen T, Cidlowski J A. Antiinflammatory action of glucocorticoids—new mechanisms for old drugs. N Engl J Med. 2005 Oct. 21; 353(16):1711-1723.

Schmidhammer R, Wassermann E, Germann P, Redl H, Ullrich R. Infusion of increasing doses of endotoxin induces progressive acute lung injury but prevents early pulmonary hypertension in pigs. Shock. 2006 May 4; 25(4):389-394.

Smith C W, Rothlein R, Hughes B J, Mariscalco M M, Rudloff H E, Schmalstieg F C, et al. Recognition of an endothelial determinant for CD 18-dependent human neutrophil adherence and transendothelial migration. J Clin Invest. American Society for Clinical Investigation; 1988 November; 82(11):1746-1756.

Soerensen K E, Olsen H G, Skovgaard K, Wiinberg B, Nielsen O L, Leifsson P S, et al. Disseminated Intravascular Coagulation in a Novel Porcine Model of Severe *Staphylococcus aureus* Sepsis Fulfills Human Clinical Criteria. J Comp Pathol. 2013 November; 149(4):463-474.

Sun C, Beard R S, McLean D L, Rigor R R, Konia T, Wu M H, et al. ADAM15 deficiency attenuates pulmonary hyperpermeability and acute lung injury in lipopolysaccharide-treated mice. Am J Physiol Lung Cell Mol Physiol. 2012 Nov. 16;.

Satelli, A., J. Hu, X. Xia, and S. Li. 2016. Potential Function of Exogenous Vimentin on the Activation of Wnt Signaling Pathway in Cancer Cells. *J Cancer* 7: 1824-1832.

Thorlacius, H., L. Lindbom, and J. Raud. 1997. Cytokine-induced leukocyte rolling in mouse cremaster muscle arterioles in P-selectin dependent. *Am J Physiol* 272: H1725-1729.

Timpa, A. R. Kurundkar, D. W. Holt, D. R. Kelly, Y. E. Hartman, M. L. Neel, R. K. Karnatak, R. L. Schelonka, G. M. Anantharamaiah, C. R. Killingsworth, and A. Maheshwari. 2010. Plasma concentrations of inflammatory cytokines rise rapidly during ECMO-related SIRS due to the release of preformed stores in the intestine. *Lab Invest* 90: 128-139.

Wilkins, P. P., R. P. McEver, and R. D. Cummings. 1996. Structures of the O-glycans on P-selectin glycoprotein ligand-1 from HL-60 cells. *J Biol Chem* 271: 18732-18742.

Xiao H, Siddiqui J, Remick D G. Mechanisms of mortality in early and late sepsis. Infect Immun. 2006 September; 74(9):5227-5235.

Zarbock A, Singbartl K, Ley K. Complete reversal of acid-induced acute lung injury by blocking of platelet-neutrophil aggregation. J Clin Invest. 2006 December; 116 (12):3211-3219.

Zarbock A, Polanowska-Grabowska R K, Ley K. Platelet-neutrophil-interactions: linking hemostasis and inflammation. Blood Rev. 2007 March; 21(2):99-111.

The scope of the present application is not intended to be limited to the particular embodiments of the process, machine, manufacture, composition of matter, means, methods and steps described in the specification.

---

What is claimed is:

1. A method of treating or preventing acute inflammation in an individual, comprising the step of delivering to the individual a therapeutically effective amount of vimentin (SEQ ID NO: 1) or a functionally active fragment of vimentin or variant thereof, wherein the fragment is no more than 400 amino acids in length and comprises the sequence FANYIDKVRF-LEQQNKILLAELEQLKGQGK.

2. The method of claim 1, wherein the acute inflammation comprises acute lung injury, secondary lung injury, acute respiratory distress syndrome, ischemia/reperfusion injury, trauma, sepsis, pancreatitis, drug-induced organ injury, or a combination thereof.

3. The method of claim 1, wherein the individual has acute lung injury or acute respiratory distress syndrome.

4. The method of claim 1, wherein the individual is provided a second therapy for the medical condition.

5. The method of claim 1, wherein the method further comprises diagnosis of the medical condition.

6. The method of claim 1, wherein the fragment of vimentin is delivered to the individual intravenously, intradermally, transdermally, intrathecally, intraarterially, intraperitoneally, intranasally, intravaginally, intrarectally, topically, intramuscularly, subcutaneously, mucosally, orally, topically, locally, by inhalation, by injection, by infusion, via catheter, and/or via lavage.

7. The method of claim 1, wherein the fragment of vimentin is delivered to the individual multiple times.

8. The method of claim 7, wherein the fragment of vimentin is delivered to the individual once a day, more than once a day, more than once a week, more than once a month, or more than once a year.

9. The method of claim 1, wherein the fragment of vimentin is provided to the individual by constant infusion.

10. The method of claim 1, wherein the wherein the fragment is no more than 30, 40, or 50 amino acids in length.

* * * * *

SEQUENCE LISTING

```
<160> NUMBER OF SEQ ID NOS: 8

<210> SEQ ID NO 1
<211> LENGTH: 466
<212> TYPE: PRT
<213> ORGANISM: Homo sapiens

<400> SEQUENCE: 1

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
        130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175
```

```
Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
    260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465

<210> SEQ ID NO 2
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 2

Phe Lys Asn Thr Arg Thr Asn Glu Lys Val Glu Leu Gln Glu Leu Asn
1               5                   10                  15

Asp Arg Phe Ala Asn Tyr Ile Asp Lys Val Arg Phe Leu Glu Gln Gln
            20                  25                  30

Asn Lys Ile Leu Leu Ala Glu Leu Glu Gln Leu Lys Gly Gln Gly Lys
        35                  40                  45

Ser Arg Leu Gly Asp Leu Tyr Glu Glu Glu Met Arg Glu Leu Arg Arg
    50                  55                  60
```

-continued

```
Gln Val Asp Gln Leu Thr Asn Asp Lys Ala Arg Val Glu Val Glu Arg
 65                  70                  75                  80

Asp Asn Leu Ala Glu Asp Ile Met Arg Leu Arg Glu Lys Leu Gln Glu
                 85                  90                  95

Glu Met Leu Gln Arg Glu Glu Ala Glu Asn Thr Leu Gln Ser Phe Arg
            100                 105                 110

Gln Asp Val Asp Asn Ala Ser Leu Ala Arg Leu Asp Leu Glu Arg Lys
        115                 120                 125

Val Glu Ser Leu Gln Glu Ile Ala Phe Leu Lys Lys Leu His Glu
    130                 135                 140

Glu Glu Ile Gln Glu Leu Gln Ala Gln Ile Gln Glu Gln His Val Gln
145                 150                 155                 160

Ile Asp Val Asp Val Ser Lys Pro Asp Leu Thr Ala Ala Leu Arg Asp
                165                 170                 175

Val Arg Gln Gln Tyr Glu Ser Val Ala Ala Lys Asn Leu Gln Glu Ala
            180                 185                 190

Glu Glu Trp Tyr Lys Ser Lys Phe Ala Asp Leu Ser Glu Ala Ala Asn
        195                 200                 205

Arg Asn Asn Asp Ala Leu Arg Gln Ala Lys Gln Glu Ser Thr Glu Tyr
    210                 215                 220

Arg Arg Gln Val Gln Ser Leu Thr Cys Glu Val Asp Ala Leu Lys Gly
225                 230                 235                 240

Thr Asn Glu Ser Leu Glu Arg Gln Met Arg Glu Met Glu Glu Asn Phe
                245                 250                 255

Ala Val Glu Ala Ala Asn Tyr Gln Asp Thr Ile Gly Arg Leu Gln Asp
            260                 265                 270

Glu Ile Gln Asn Met Lys Glu Glu Met Ala Arg His Leu Arg Glu Tyr
        275                 280                 285

Gln Asp Leu Leu Asn Val Lys Met Ala Leu Asp Ile Glu Ile Ala Thr
    290                 295                 300

Tyr Arg Lys Leu Leu Glu Gly Glu
305                 310
```

```
<210> SEQ ID NO 3
<211> LENGTH: 82
<212> TYPE: PRT
<213> ORGANISM: Artificial Sequence
<220> FEATURE:
<223> OTHER INFORMATION: Synthetic Polypeptide

<400> SEQUENCE: 3
```

```
Met Phe Gly Gly Pro Gly Thr Ala Ser Arg Pro Ser Ser Ser Arg Ser
 1               5                  10                  15

Tyr Val Thr Thr Ser Thr Arg Thr Tyr Ser Leu Gly Ser Ala Leu Arg
                 20                  25                  30

Pro Ser Thr Ser Arg Ser Leu Tyr Ala Ser Ser Pro Gly Gly Val Tyr
            35                  40                  45

Ala Thr Arg Ser Ser Ala Val Arg Leu Arg Ser Ser Val Pro Gly Val
        50                  55                  60

Arg Leu Leu Gln Asp Ser Val Asp Phe Ser Leu Ala Asp Ala Ile Asn
 65                  70                  75                  80

Thr Glu
```

```
<210> SEQ ID NO 4
<211> LENGTH: 282
<212> TYPE: DNA
```

<213> ORGANISM: Artificial Sequence
<220> FEATURE:
<223> OTHER INFORMATION: Synthetic Nucleotide

<400> SEQUENCE: 4

```
tccaccaggt ccgtgtcctc gtcctcctac cgcaggatgt tcggcggccc gggcaccgcg      60
agccggccga gctccagccg gagctacgtg actacgtcca cccgcaccta cagcctgggc     120
agcgcgctgc gccccagcac cagccgcagc ctctacgcct cgtccccggg cggcgtgtat     180
gccacgcgct cctctgccgt gcgcctgcgg agcagcgtgc cggggtgcg gctcctgcag      240 gactcggtgg acttctcgct ggccgacgcc atcaacaccg ag                        282
```

<210> SEQ ID NO 5
<211> LENGTH: 312
<212> TYPE: PRT
<213> ORGANISM: Artificial Sequence
<220> FEATURE:
<223> OTHER INFORMATION: Synthetic Polypeptide

<400> SEQUENCE: 5

```
Phe Lys Asn Thr Arg Thr Asn Glu Lys Val Glu Leu Gln Glu Leu Asn
1               5                   10                  15

Asp Arg Phe Ala Asn Tyr Ile Asp Lys Val Arg Phe Leu Glu Gln Gln
            20                  25                  30

Asn Lys Ile Leu Leu Ala Glu Leu Glu Gln Leu Lys Gly Gln Gly Lys
        35                  40                  45

Ser Arg Leu Gly Asp Leu Tyr Glu Glu Glu Met Arg Glu Leu Arg Arg
    50                  55                  60

Gln Val Asp Gln Leu Thr Asn Asp Lys Ala Arg Val Glu Val Glu Arg
65                  70                  75                  80

Asp Asn Leu Ala Glu Asp Ile Met Arg Leu Arg Glu Lys Leu Gln Glu
                85                  90                  95

Glu Met Leu Gln Arg Glu Glu Ala Glu Asn Thr Leu Gln Ser Phe Arg
            100                 105                 110

Gln Asp Val Asp Asn Ala Ser Leu Ala Arg Leu Asp Leu Glu Arg Lys
        115                 120                 125

Val Glu Ser Leu Gln Glu Glu Ile Ala Phe Leu Lys Lys Leu His Glu
    130                 135                 140

Glu Glu Ile Gln Glu Leu Gln Ala Gln Ile Gln Glu Gln His Val Gln
145                 150                 155                 160

Ile Asp Val Asp Val Ser Lys Pro Asp Leu Thr Ala Ala Leu Arg Asp
                165                 170                 175

Val Arg Gln Gln Tyr Glu Ser Val Ala Ala Lys Asn Leu Gln Glu Ala
            180                 185                 190

Glu Glu Trp Tyr Lys Ser Lys Phe Ala Asp Leu Ser Glu Ala Ala Asn
        195                 200                 205

Arg Asn Asn Asp Ala Leu Arg Gln Ala Lys Gln Glu Ser Thr Glu Tyr
    210                 215                 220

Arg Arg Gln Val Gln Ser Leu Thr Cys Glu Val Asp Ala Leu Lys Gly
225                 230                 235                 240

Thr Asn Glu Ser Leu Glu Arg Gln Met Arg Glu Met Glu Glu Asn Phe
                245                 250                 255

Ala Val Glu Ala Ala Asn Tyr Gln Asp Thr Ile Gly Arg Leu Gln Asp
            260                 265                 270

Glu Ile Gln Asn Met Lys Glu Glu Met Ala Arg His Leu Arg Glu Tyr
        275                 280                 285
```

Gln Asp Leu Leu Asn Val Lys Met Ala Leu Asp Ile Glu Ile Ala Thr
    290                 295                 300

Tyr Arg Lys Leu Leu Glu Gly Glu
305                 310

<210> SEQ ID NO 6
<211> LENGTH: 936
<212> TYPE: DNA
<213> ORGANISM: Artificial Sequence
<220> FEATURE:
<223> OTHER INFORMATION: Synthetic Nucleotide

<400> SEQUENCE: 6

| | | | | | | |
|---|---|---|---|---|---|---|
| ttcaagaaca | cccgcaccaa | cgagaaggtg | gagctgcagg | agctgaatga | ccgcttcgcc | 60 |
| aactacatcg | acaaggtgcg | cttcctggag | cagcagaata | agatcctgct | ggccgagctc | 120 |
| gagcagctca | agggccaagg | caagtcgcgc | ctggggacc | tctacgagga | ggagatgcgg | 180 |
| gagctgcgcc | ggcaggtgga | ccagctaacc | aacgacaaag | cccgcgtcga | ggtggagcgc | 240 |
| gacaacctgg | ccgaggacat | catgcgcctc | cgggagaaat | tgcaggagga | gatgcttcag | 300 |
| agagaggaag | ccgaaaacac | cctgcaatct | ttcagacagg | atgttgacaa | tgcgtctctg | 360 |
| gcacgtcttg | accttgaacg | caaagtggaa | tctttgcaag | aagagattgc | ctttttgaag | 420 |
| aaactccacg | aagaggaaat | ccaggagctg | caggctcaga | ttcaggaaca | gcatgtccaa | 480 |
| atcgatgtgg | atgtttccaa | gcctgacctc | acggctgccc | tgcgtgacgt | acgtcagcaa | 540 |
| tatgaaagtg | tggctgccaa | gaacctgcag | gaggcagaag | aatggtacaa | atccaagttt | 600 |
| gctgacctct | ctgaggctgc | caaccggaac | aatgacgccc | tgcgccaggc | aaagcaggag | 660 |
| tccactgagt | accggagaca | ggtgcagtcc | ctcacctgtg | aagtggatgc | ccttaaagga | 720 |
| accaatgagt | ccctggaacg | ccagatgcgt | gaaatggaag | agaactttgc | cgttgaagct | 780 |
| gctaactacc | aagacactat | tggccgcctg | caggatgaga | ttcagaatat | gaaggaggaa | 840 |
| atggctcgtc | accttcgtga | ataccaagac | ctgctcaatg | ttaagatggc | ccttgacatt | 900 |
| gagattgcca | cctacaggaa | gctgctggaa | ggcgag | | | 936 |

<210> SEQ ID NO 7
<211> LENGTH: 59
<212> TYPE: PRT
<213> ORGANISM: Artificial Sequence
<220> FEATURE:
<223> OTHER INFORMATION: Synthetic Polypeptide

<400> SEQUENCE: 7

Glu Ser Arg Ile Ser Leu Pro Leu Pro Asn Phe Ser Ser Leu Asn Leu
1               5                   10                  15

Arg Glu Thr Asn Leu Asp Ser Leu Pro Leu Val Asp Thr His Ser Lys
            20                  25                  30

Arg Thr Leu Leu Ile Lys Thr Val Glu Thr Arg Asp Gly Gln Val Ile
        35                  40                  45

Asn Glu Thr Ser Gln His His Asp Asp Leu Glu
    50                  55

<210> SEQ ID NO 8
<211> LENGTH: 180
<212> TYPE: DNA
<213> ORGANISM: Artificial Sequence
<220> FEATURE:
<223> OTHER INFORMATION: Synthetic Nucleotide

```
<400> SEQUENCE: 8
gagagcagga tttctctgcc tcttccaaac ttttcctccc tgaacctgag ggaaactaat      60
ctggattcac tccctctggt tgatacccac tcaaaaagga cacttctgat taagacggtt     120
gaaactagag atggacaggt tatcaacgaa acttctcagc atcacgatga ccttgaataa     180
```